United States Patent
Karavitis et al.

(10) Patent No.: US 11,738,206 B2
(45) Date of Patent: *Aug. 29, 2023

(54) SYSTEMS AND METHODS FOR CONTROLLING THERAPEUTIC LASER PULSE DURATION

(71) Applicant: Cutera, Inc., Brisbane, CA (US)

(72) Inventors: Michael A. Karavitis, San Pedro, CA (US); Wytze E. van der Veer, San Bruno, CA (US); Amogh Kothare, Fremont, CA (US); Soenke A. Moeller, Berkeley, CA (US); Shawn M. Gilliam, Daly City, CA (US)

(73) Assignee: CUTERA, INC., Brisbane, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 17/120,159

(22) Filed: Dec. 12, 2020

(65) Prior Publication Data

US 2021/0268305 A1   Sep. 2, 2021

Related U.S. Application Data

(63) Continuation of application No. 16/805,761, filed on Feb. 29, 2020, now Pat. No. 10,864,380.

(51) Int. Cl.
*A61B 18/20* (2006.01)
*A61N 5/06* (2006.01)
(Continued)

(52) U.S. Cl.
CPC ............ *A61N 5/0616* (2013.01); *A61B 18/20* (2013.01); *A61B 2017/00057* (2013.01);
(Continued)

(58) Field of Classification Search
CPC ........ A61B 18/20; A61B 18/203; A61N 5/06; A61N 5/0616
(Continued)

(56) References Cited

U.S. PATENT DOCUMENTS 5,520,679 A   5/1996 Lin
5,662,643 A   9/1997 Kung et al.
(Continued)

FOREIGN PATENT DOCUMENTS

WO   1999049937 A1   10/1999
WO   2007127924 A2   11/2007
(Continued)

OTHER PUBLICATIONS

Anderson, Rox R. et al., "Selective Photothermolysis of Lipid-Rich Tissues: A Free Electron Laser Study," Lasers in Surgery & Medicine 38:913-919 (2006), Wiley Interscience.
(Continued)

*Primary Examiner* — Lynsey C Eiseman
(74) *Attorney, Agent, or Firm* — Timothy L. Scott, Esq.

(57) ABSTRACT

Dermatological systems and methods for providing a therapeutic laser treatment wherein the duration of a therapeutic laser pulse is based on one or more determinations of a surface temperature of the skin during the delivery of the pulse. Initiation of the therapeutic laser pulse may be based on sensed skin temperature during a cooling of the skin prior to initiation of the pulse.

13 Claims, 12 Drawing Sheets

1210  Initiate the application of a therapeutic laser pulse to a target skin area of a patient at a first timepoint 1220  Determine a surface temperature of the target skin area at least once during the application of the therapeutic laser pulse based at least in part on infrared energy radiated from the target skin area 1230  Terminate the application of the therapeutic laser pulse to the target skin area at a second timepoint based on the at least one surface temperature determination

(51) Int. Cl.
- *A61N 5/00* (2006.01)
- *A61B 17/00* (2006.01)
- *A61B 18/00* (2006.01)
- *A61N 5/067* (2006.01)

(52) U.S. Cl.
CPC ........... *A61B 2017/00154* (2013.01); *A61B 2018/00761* (2013.01); *A61B 2018/00791* (2013.01); *A61N 5/067* (2021.08); *A61N 2005/007* (2013.01); *A61N 2005/0644* (2013.01); *A61N 2005/0659* (2013.01)

(58) Field of Classification Search
USPC .......................................................... 606/9
See application file for complete search history.

(56) References Cited

U.S. PATENT DOCUMENTS

| | | | |
|---|---|---|---|
| 5,769,847 A | 6/1998 | Panescu et al. | |
| 5,782,822 A | 7/1998 | Telfair et al. | |
| 5,976,123 A * | 11/1999 | Baumgardner | A61B 18/203 606/13 |
| 5,979,454 A | 11/1999 | Anvari et al. | |
| 6,015,404 A | 1/2000 | Altshuler et al. | |
| 6,026,816 A | 2/2000 | McMillan et al. | |
| 6,142,939 A | 11/2000 | Eppstein et al. | |
| 6,200,308 B1 | 3/2001 | Pope et al. | |
| 6,210,426 B1 | 4/2001 | Cho et al. | |
| 6,235,016 B1 | 5/2001 | Stewart | |
| 6,328,733 B1 | 12/2001 | Trost | |
| 6,408,212 B1 | 6/2002 | Neev | |
| 6,451,010 B1 | 9/2002 | Angeley | |
| 6,488,696 B1 | 12/2002 | Cho et al. | |
| 6,508,813 B1 | 1/2003 | Altshuler | |
| 6,514,244 B2 | 2/2003 | Pope et al. | |
| 6,517,532 B1 | 2/2003 | Altshuler et al. | |
| 6,527,797 B1 | 3/2003 | Masotti et al. | |
| 6,605,080 B1 | 8/2003 | Altshuler et al. | |
| 6,632,219 B1 | 10/2003 | Baranov et al. | |
| 6,638,272 B2 | 10/2003 | Cho et al. | |
| 6,663,620 B2 | 12/2003 | Altshuler et al. | |
| 6,692,517 B2 | 2/2004 | Cho et al. | |
| 6,702,838 B1 | 3/2004 | Andersen et al. | |
| 6,723,090 B2 | 4/2004 | Altshuler et al. | |
| 6,743,222 B2 | 6/2004 | Durkin et al. | |
| 6,758,845 B1 | 7/2004 | Weckwerth et al. | |
| 6,770,069 B1 | 8/2004 | Hobart et al. | |
| 6,835,202 B2 | 12/2004 | Harth et al. | |
| 6,887,233 B2 | 5/2005 | Angeley et al. | |
| D507,654 S | 7/2005 | Gollnick et al. | |
| 6,951,558 B2 | 10/2005 | Angeley et al. | |
| 6,976,985 B2 | 12/2005 | Altshuler et al. | |
| 6,991,644 B2 | 1/2006 | Spooner et al. | |
| 6,997,923 B2 | 2/2006 | Anderson et al. | |
| 7,018,396 B2 | 3/2006 | Sierra et al. | |
| 7,044,959 B2 | 3/2006 | Anderson et al. | |
| 7,041,094 B2 | 5/2006 | Connors et al. | |
| 7,060,061 B2 | 6/2006 | Altshuler et al. | |
| 7,184,614 B2 | 2/2007 | Slatkine | |
| 7,198,634 B2 | 4/2007 | Harth et al. | |
| 7,204,832 B2 | 4/2007 | Altshuler et al. | |
| 7,208,007 B2 | 4/2007 | Nightingale et al. | |
| 7,245,369 B2 | 7/2007 | Wang et al. | |
| 7,250,047 B2 | 7/2007 | Anderson et al. | |
| 7,291,140 B2 | 11/2007 | MacFarland et al. | |
| 7,326,199 B2 | 2/2008 | MacFarland et al. | |
| 7,331,953 B2 | 2/2008 | Manstein et al. | |
| 7,351,252 B2 | 4/2008 | Altshuler et al. | |
| 7,367,341 B2 | 5/2008 | Anderson et al. | |
| RE40,403 E | 6/2008 | Cho et al. | |
| 7,427,289 B2 | 9/2008 | Sierra et al. | |
| 7,438,713 B2 | 10/2008 | Angeley et al. | |
| 7,465,307 B2 | 12/2008 | Connors et al. | |
| 7,470,270 B2 | 12/2008 | Azar et al. | |
| 7,524,328 B2 | 4/2009 | Connors et al. | |
| 7,618,414 B2 | 11/2009 | Connors et al. | |
| 7,671,327 B2 | 3/2010 | Clancy et al. | |
| 7,703,458 B2 | 4/2010 | Levernier et al. | |
| 7,722,600 B2 | 5/2010 | Connors et al. | |
| 7,731,953 B2 | 6/2010 | Leonard et al. | |
| 7,762,964 B2 | 7/2010 | Slatkine | |
| 7,762,965 B2 | 7/2010 | Slatkine | |
| 7,763,016 B2 | 7/2010 | Altshuler et al. | |
| 7,771,374 B2 | 8/2010 | Slatkine | |
| 7,780,652 B2 | 8/2010 | MacFarland et al. | |
| 7,814,915 B2 | 10/2010 | Davenport et al. | |
| 7,824,396 B2 | 11/2010 | Angeley et al. | |
| 7,878,206 B2 | 2/2011 | Connors et al. | |
| 7,891,362 B2 | 2/2011 | Domankevitz et al. | |
| 7,942,153 B2 | 5/2011 | Manstein et al. | |
| 7,975,702 B2 | 7/2011 | Cho et al. | |
| D643,530 S | 8/2011 | Ramstad et al. | |
| 7,998,181 B2 | 8/2011 | Nightingale et al. | |
| 8,002,768 B1 | 8/2011 | Altshuler et al. | |
| 8,113,209 B2 | 2/2012 | Masotti et al. | |
| 8,172,835 B2 | 5/2012 | Leyh et al. | |
| 8,182,473 B2 | 5/2012 | Altshuler et al. | |
| 8,190,243 B2 | 5/2012 | Welches et al. | |
| 8,211,097 B2 | 7/2012 | Leyh | |
| 8,216,215 B2 | 7/2012 | Flyash et al. | |
| 8,244,369 B2 | 8/2012 | Kreindel | |
| 8,276,592 B2 | 10/2012 | Davenport et al. | |
| 8,285,390 B2 | 10/2012 | Levinson et al. | |
| 8,317,779 B2 | 11/2012 | Mirkov et al. | |
| 8,317,780 B2 | 11/2012 | Davenport et al. | |
| 8,322,348 B2 | 12/2012 | Mirkov et al. | |
| 8,328,796 B2 | 12/2012 | Altshuler et al. | |
| 8,353,899 B1 | 1/2013 | Wells et al. | |
| 8,366,703 B2 | 2/2013 | Davenport et al. | |
| 8,439,901 B2 | 5/2013 | Davenport et al. | |
| 8,454,591 B2 | 6/2013 | Leyh et al. | |
| 8,460,280 B2 | 6/2013 | Davenport et al. | |
| 8,474,463 B2 | 7/2013 | Levernier et al. | |
| 8,506,506 B2 | 8/2013 | Nebrigic et al. | |
| 8,523,927 B2 | 9/2013 | Levinson et al. | |
| 8,562,599 B2 | 10/2013 | Leyh | |
| 8,585,618 B2 | 11/2013 | Hunziker et al. | |
| 8,656,931 B2 | 2/2014 | Davenport et al. | |
| 8,702,769 B2 | 4/2014 | Eckhouse et al. | |
| 8,702,774 B2 | 4/2014 | Baker et al. | |
| 8,728,064 B2 | 5/2014 | Schomacker et al. | |
| 8,771,263 B2 | 7/2014 | Epshtein et al. | |
| 8,778,003 B2 | 7/2014 | Eckhouse et al. | |
| 8,834,547 B2 | 9/2014 | Anderson et al. | |
| 8,840,608 B2 | 9/2014 | Anderson et al. | |
| 8,870,856 B2 | 10/2014 | Connors et al. | |
| 8,876,809 B2 | 11/2014 | Eckhouse et al. | |
| 8,876,811 B2 | 11/2014 | Lewinsky et al. | |
| 8,882,753 B2 | 11/2014 | Mehta et al. | |
| 8,915,906 B2 | 12/2014 | Davenport et al. | |
| 8,915,948 B2 | 12/2014 | Altshuler et al. | |
| 8,920,409 B2 | 12/2014 | Davenport et al. | |
| 8,932,278 B2 | 1/2015 | Tankovich et al. | |
| 8,936,593 B2 | 1/2015 | Epshtein et al. | |
| 9,078,681 B2 | 7/2015 | Koifman et al. | |
| 9,078,683 B2 | 7/2015 | Sabati et al. | |
| 9,084,587 B2 | 7/2015 | Eckhouse et al. | |
| 9,132,031 B2 | 9/2015 | Levinson et al. | |
| 9,149,332 B2 | 10/2015 | Koifman et al. | |
| 9,161,802 B2 | 10/2015 | Przybyszewski | |
| 9,271,793 B2 | 3/2016 | Eckhouse et al. | |
| 9,308,120 B2 | 4/2016 | Anderson et al. | |
| 9,333,379 B2 | 5/2016 | Azoulay | |
| 9,345,531 B2 | 5/2016 | Furnish et al. | |
| D759,236 S | 6/2016 | Preiss et al. | |
| 9,358,068 B2 | 6/2016 | Schomacker et al. | |
| 9,375,345 B2 | 6/2016 | Levinson et al. | |
| 9,486,285 B2 | 11/2016 | Paithankar et al. | |
| 9,539,439 B2 | 1/2017 | Jones et al. | |
| 9,597,528 B2 | 3/2017 | Schomacker et al. | |
| 9,685,753 B2 | 6/2017 | Hellstrom et al. | |
| 9,907,612 B2 | 3/2018 | Bradley | |
| 9,913,688 B1 | 3/2018 | Karavitis | |
| 9,949,877 B2 | 4/2018 | Rubinchik et al. | |

(56) References Cited

U.S. PATENT DOCUMENTS

| | | | |
|---|---|---|---|
| 9,962,220 B2 | 5/2018 | Domankevitz | |
| 10,069,272 B2 | 9/2018 | Bhawalkar et al. | |
| 10,085,814 B2 | 10/2018 | Azoulay | |
| 10,149,984 B2 | 12/2018 | Modi et al. | |
| 10,305,244 B2 | 5/2019 | Sierra et al. | |
| 10,426,564 B2 | 10/2019 | Azoulay | |
| 10,434,324 B2 | 10/2019 | Mikrov et al. | |
| 10,448,961 B2 | 10/2019 | Preiss et al. | |
| 10,478,264 B2 | 11/2019 | Azoulay | |
| 10,492,862 B2 | 12/2019 | Domankevitz | |
| 10,517,676 B2 | 12/2019 | Schuster | |
| 10,561,464 B2 | 2/2020 | Koifman et al. | |
| 10,561,570 B2 | 2/2020 | Eckhouse et al. | |
| D878,554 S | 3/2020 | Preiss et al. | |
| 10,622,780 B2 | 4/2020 | Shang et al. | |
| 10,624,699 B2 | 4/2020 | Schomacker et al. | |
| 10,729,496 B2 | 8/2020 | Hunziker et al. | |
| 10,864,380 B1 | 12/2020 | Karavitis et al. | |
| 2001/0007068 A1* | 7/2001 | Ota | A61B 18/203 606/9 |
| 2002/0035360 A1 | 3/2002 | Connors et al. | |
| 2002/0091377 A1 | 7/2002 | Anderson et al. | |
| 2002/0123745 A1 | 9/2002 | Svaasand et al. | |
| 2002/0161357 A1 | 10/2002 | Anderson et al. | |
| 2002/0173782 A1 | 11/2002 | Cense et al. | |
| 2003/0032950 A1 | 2/2003 | Altshuler et al. | |
| 2003/0199859 A1 | 10/2003 | Altshuler et al. | |
| 2004/0034319 A1 | 2/2004 | Anderson | |
| 2004/0034341 A1 | 2/2004 | Altshuler et al. | |
| 2004/0073079 A1 | 4/2004 | Altshuler et al. | |
| 2004/0093042 A1 | 5/2004 | Altshuler et al. | |
| 2004/0167499 A1 | 8/2004 | Grove et al. | |
| 2005/0171581 A1 | 8/2005 | Connors et al. | |
| 2005/0215988 A1 | 9/2005 | Altshuler et al. | |
| 2005/0251118 A1 | 11/2005 | Anderson et al. | |
| 2006/0122668 A1 | 6/2006 | Anderson et al. | |
| 2007/0073308 A1 | 3/2007 | Anderson et al. | |
| 2007/0213695 A1 | 9/2007 | Perl et al. | |
| 2008/0009842 A1 | 1/2008 | Manstein et al. | |
| 2008/0009923 A1 | 1/2008 | Paithankar et al. | |
| 2008/0058784 A1 | 3/2008 | Manstein et al. | |
| 2008/0080585 A1 | 4/2008 | Glebov et al. | |
| 2008/0188914 A1 | 8/2008 | Gustavsson | |
| 2008/0214988 A1 | 9/2008 | Altshuler et al. | |
| 2008/0215040 A1 | 9/2008 | Paithankar et al. | |
| 2008/0319430 A1 | 12/2008 | Zenzie et al. | |
| 2009/0024193 A1 | 1/2009 | Altshuler et al. | |
| 2009/0069871 A1 | 3/2009 | Mahadevan-Jansen et al. | |
| 2009/0105699 A1 | 4/2009 | Angeley et al. | |
| 2009/0112192 A1 | 4/2009 | Barolet et al. | |
| 2009/0182397 A1 | 7/2009 | Gustavsson | |
| 2010/0049178 A1 | 2/2010 | Deem et al. | |
| 2010/0179521 A1 | 7/2010 | Ghaffari | |
| 2010/0249772 A1* | 9/2010 | Mehta | A61B 18/14 606/41 |
| 2011/0137230 A1 | 6/2011 | Altshuler et al. | |
| 2012/0022518 A1 | 1/2012 | Levinson | |
| 2012/0116271 A1 | 5/2012 | Caruso et al. | |
| 2013/0060309 A1 | 3/2013 | Bradley | |
| 2013/0066309 A1 | 3/2013 | Levinson | |
| 2013/0079684 A1 | 6/2013 | Rosen et al. | |
| 2013/0184693 A1 | 7/2013 | Neev | |
| 2014/0005760 A1 | 1/2014 | Levinson et al. | |
| 2014/0257443 A1 | 9/2014 | Baker et al. | |
| 2014/0277219 A1 | 9/2014 | Nanda | |
| 2014/0277302 A1 | 9/2014 | Weber et al. | |
| 2014/0316393 A1 | 10/2014 | Levinson | |
| 2014/0379052 A1 | 12/2014 | Myeong et al. | |
| 2015/0202454 A1 | 7/2015 | Burnett | |
| 2015/0216816 A1 | 8/2015 | O'Neil et al. | |
| 2015/0223975 A1 | 8/2015 | Anderson et al. | |
| 2015/0265492 A1 | 9/2015 | Eckhouse et al. | |
| 2015/0328077 A1 | 11/2015 | Levinson | |
| 2016/0051401 A1 | 2/2016 | Yee et al. | |
| 2016/0310756 A1 | 10/2016 | Boll et al. | |
| 2017/0063468 A1 | 3/2017 | Guo et al. | |
| 2017/0304645 A1 | 10/2017 | Schomacker | |
| 2018/0036029 A1 | 2/2018 | Anderson et al. | |
| 2018/0071024 A1 | 3/2018 | Harris | |
| 2018/0140866 A1* | 5/2018 | Daly | A61B 18/203 |
| 2018/0177550 A1 | 6/2018 | Anderson et al. | |
| 2019/0000529 A1 | 1/2019 | Kothare et al. | |
| 2019/0374791 A1 | 12/2019 | Tagliaferri et al. | |

FOREIGN PATENT DOCUMENTS

| | | |
|---|---|---|
| WO | 2008039557 A1 | 4/2008 |
| WO | 2008143678 A1 | 11/2008 |
| WO | 2014149021 A2 | 9/2014 |
| WO | 2014151872 A2 | 9/2014 |

OTHER PUBLICATIONS

Bashkatov, A. N., "Optical Properties of Human Skin, Subcutaneous and Mucous Tissues in the Wavelength Range From 400 to 2000 nm," J. Phys D: Appl. Phys., vol. 38, 2543-2555 (2005), Institute of Physics Publishing, UK.

Dewhirst, M.W. et al., "Basic Principles of Thermal Dosimetry and Thermal Thresholds for Tissue Damage from Hyperthermia," Int. J. Hyperthermia, vol. 19 No. 3, May-Jun. 2003, 267-294, T&F Online, UK.

Jacques, Steven L., and Daniel J. McAuliffe, "The Melanosome: Threshold Temperature For Explosive Vaporization and Internal Absorption Coefficient During Pulsed Laser Irradiation," Photochemistry and Photobiology, vol. 53, No. 6, 769-775 (1991), Pergamon Press plc, UK.

Keller, M. D. et al., "In Vitro Testing of Dual-Mode Thulium Microsurgical Laser," Photonic Therapeutics and Diagnostics VIII, ed. N. Kollias et al., Proc. of SPIE, vol. 8207, 820711-1 through 820711-8, 2012.

Li, X. C. et al., "Optical Properties of Edible Oils Within Spectral Range From 300 to 2500 nm Determined by Double Optical Pathlength Transmission Method," Applied Optics, vol. 54, No. 13, May 1, 2015, Optical Society of America, US.

Lloyd, Jenifer R., and Mirko Mirkov, "Selective Photothermolysis of the Sebaceious Glands for Acne Treatment," Lasers in Surgery and Medicine, vol. 31, 115-120 (2002), Wiley-Liss, Inc.

Paithankar, Dilip Y. et al., "Acne Treatment With a 1,450 nm Wavelength Laser and Cryogen Spray Cooling," Lasers in Surgery and Medicine, vol. 31, 106-114 (2002), Wiley-Liss, Inc.

Paithankar, Dilip Y. et al., "Subsurface Skin Renewal by Treatment With a 1450-nm Laser in Combination With Dynamic Cooling," Journal of Biomedical Optics, vol. 8, No. 3, 545-551, Jul. 2003 Lasers in Surgery and Medicine, vol. 31, 106-114 (Jul. 2003), SPIE.

Pearce, John A., "Relationship Between Arrhenius Models of Thermal Damage and the CEM 43 Thermal Dose," in Energy-Based Treatment of Tissue and Assessment V, ed. Thomas P. Ryan, Proc of SPIE vol. 7181, 718104-1 through 718104-15 (2009), SPIE.

Sakamoto, Fernanda H. et al., "Selective Photothermolysis to Target Sebaceous Glands: Theoretical Estimation of Parameters and Preliminary Results Using a Free Electron Laser," Lasers in Surgery and Medicine, vol. 44, 175-183 (2012), Wiley Periodicals, Inc.

Salomatina, Elena et al., "Optical Properties of Normal and Cancerous Human Skin in the Visible and Near-Infrared Spectral Range," J. Biomed Optics., 11 (6), Nov./Dec. 2006, 064026-1 through 064026-9, SPIE.

Tanghetti, Emil, Oral presentation, "A Histological Evaluation of Sebaceous Gland Damage With a 1726 nm Laser," Abstract Session, Clinical Applications-Cutaneous, Mar. 29, 2019, ASLMS 2019, Americal Society for Laser Medicine & Surgery, Inc.

Tanghetti, Emil, Oral presentation, "Laser Destruction of Sebaceous Glands: Threading the Needle," Special Sessions (CME), Cutting Edge: Laser and Skin, Mar. 30, 2019, ASLMS 2019, Americal Society for Laser Medicine & Surgery, Inc.

Ueno, Koichiro et al., "InSb Mid-Infrared Photon Detector for Room-Temperature Operation," Jpn. J. App. Phys., vol. 52, 092202-1 through 092202-6 (2013), The Japan Society of Applied Physics, Japan.

(56) References Cited

OTHER PUBLICATIONS

Vogel, Alfred et al., "Minimization of Thermomechanical Side Effects and Increase of Ablation Efficiency in IR Ablation by Use of Multiply Q-Switched Laser Pulses," Proc. SPIE vol. 4617A, Laser Tissue Interaction XIII, 2002.
Wang, Lihong et al., "Monte Carol Modeling of Light Transport in Multi-layered Tissues in Standard C," University of Texas M.D. Anderson Cancer Center, XX-YY (1992), Dept. of the Navy, US.
Nelson, J. Stuart et al., "Dynamic Epidermal Cooling During Pulsed Laser Treatment of Port-Wine Stain," Archives of Dermatology, vol. 131, Jun. 1995, 695-700, Americal Medical Association, US.
Saccomandi, Paola et al., "Techniques for Temperature Monitoring During Laser-Induced Thermotherapy: An Overview," International Journal of Hyperthermia, vol. 29, No. 7, Sep. 13, 2019, 609-619, Informa UK Ltd, UK.
Interlink Electronics, "Enhancing Medical Devicesand Personal Healthcare Products with Force Sensing Technology", Feb. 2014, found at: https://www.interlinkelectronics.com/.
Suprapto, S.S. et al., "Low-Cost Pressure Sensor Matrix Using Velostat" 2017 5th ICICI-BME, Bandung, Nov. 6-7, 2017.
Valle-Lopera, Diego Andres et al., "Test and Fabrication of Piezoresistive Sensors for Contact Pressure Measurement" Revista Facultad de Ingenieria, Medellin, Colombia, 82, pp. 47-52, 2017.

Vaissie, Laurent et al., "Bright Laser Diodes Combat Cancer", Bio Optics World, Jul./Aug. 2009.
Thompson, Daniel J., et al., "Narrow Linewidth Tunable External Cavity Diode Laser Using Wide Bandwith Filter", Rev. Sci. Instrum. 83, 023107 (2012).
Ricci, L. et al., "A Compact Grating-Stabilized Diode Laser System for Atomic Physics" Optics Communications, 117 pp. 541-549, 1995.
Wenzel, H. et al., "Design and Realization of High-Power DFB Lasers", Proceedings of SPIE, vol. 5594, Bellingham, WA, pp. 110-123, 2004.
Office Action dated May 15, 2020, U.S. Appl. No. 16/805,761, filed Feb. 29, 2020.
Notice of Allowance dated Aug. 13, 2020, U.S. Appl. No. 16/805,761, filed Feb. 29, 2020.
Tekscan, "Best Practices in Electrical Integration of the FlexiForce Sensor", 2020, found at: https://www.tekscan.com/products-solutions/sensors.
Interlink Electronics, "FSR 400 Series Data Sheet", 2020, found at: https://www.interlinkelectronics.com/.
Tekscan, "Best Practices in Mechanical Integration of the FlexiForce Sensor", 2020 found at: https://www.tekscan.com/products-solutions/sensors.

* cited by examiner

SYSTEMS AND METHODS FOR CONTROLLING THERAPEUTIC LASER PULSE DURATION

CROSS-REFERENCE TO RELATED APPLICATION

This application is a continuation of and claims the benefit of priority to U.S. patent application Ser. No. 16/805,761, filed Feb. 29, 2020, entitled "Systems and Methods for Controlling Therapeutic Laser Pulse Duration," now U.S. Pat. No. 10,864,380, which is incorporated by reference herein in its entirety.

BACKGROUND OF THE INVENTION

This invention relates generally to electromagnetic radiation-based medical treatment systems, and more specifically to systems and methods for controlling the temperature of a target skin area in the treatment of dermatological conditions. The invention includes controlling the duration of laser pulses in performing such treatment.

A variety of dermatological conditions are treatable using electromagnetic radiation (EMR). Sources of EMR in dermatological treatment systems may include, without limitation, lasers, flashlamps, and RF sources. Laser are frequently used as an EMR source to treat a range of conditions including acne vulgaris, abnormal pigmentation, vascular skin conditions (e.g., spider veins), wrinkles and fine lines, and dyschromia, and many others. Both pulsed and continuous-wave (CW) laser systems have been used, although pulsed lasers are more commonly employed.

Many dermatological EMR systems use a laser to photothermally damage a target tissue while preserving surrounding or adjacent non-targeted tissues or structures. The principle of selective photothermolysis, which involves thermally damaging a target tissue to promote a healing response, has led to the development of a variety of laser applications as standard of care in many medical fields such as ophthalmology and dermatology.

Damage to a target tissue during photothermolysis involves raising the temperature of the target tissue to a damage threshold temperature for a specified time period. For a given level of thermal damage desired, there is a tradeoff between the temperature to which the target tissue must be raised and the time that the target temperature must be maintained. The same thermal damage may be achieved using a lower temperature if the time of heating is increased; if a higher temperature is used, a shorter heating time can be used to achieve an equivalent level of thermal damage. To avoid thermal damage to non-targeted tissue, it is desirable to limit the heating time to the thermal relaxation time (TRT) of the target tissue. TRT is the time required for the target to dissipate about 63% of the thermal energy received from the pulse. It is related to the size of the target chromophore, and may range from a few nanoseconds for small chromophores such as tattoo ink particles, to hundreds of milliseconds for large chromophores such as leg venules. Accordingly, in many cases, a damage threshold temperature to achieve a desired level of thermal damage to the target tissue may be selected based on the TRT of the target tissue. For example, depending upon factors such as the laser power, fluence, spot size, etc. used in a given system, a damage threshold temperature to achieve a desired level of photothermolysis at time periods approximately equal to (e.g., slightly longer or shorter than) the TRT may be selected.

Photothermolysis can be achieved when three conditions are met: 1) the wavelength of the laser is chosen to have a preferential absorption in the target tissue over the surrounding tissue; 2) the pulse duration of the laser should be equal to or less than (=<) the thermal relaxation time (TRT) of the target tissue; and 3) the laser fluence (i.e., energy per unit area) must be sufficient to exceed the thermal damage threshold of the target tissue. Together, these principles permit laser systems to be developed that deliver energy at specific wavelengths, pulse durations, and fluences to provide controlled energy to damage target tissue while leaving non-targeted surrounding tissues and structures substantially unaffected.

Selectivity as well as overall safety would be improved if the temperature of the skin could be dynamically controlled. In particular, most laser-based dermatological treatment systems do not provide reliable control of the temperature of the skin during treatment, since pulse durations and the number of pulses applied to a target treatment area are typically selected by a user and maintained for a given treatment session until manually changed by the system user (e.g., a laser technician, physician, nurse, etc.). There is a need for laser-based treatment systems providing better control of the skin temperature. Some embodiments of the present invention achieve this by using the actual skin temperature to provide feedback to the instrument to dynamically control the temperature during a treatment.

Ideally, thermal damage is highly localized to only the particular target tissue (e.g., a particular skin layer at a particular location, or particular structures such as chromophores within a skin layer at a particular location), with nearby non-targeted tissues/structures remaining unaffected and thus available to facilitate the healing response in the targeted tissue. However, the structural complexity of the skin, which includes a variety of layers each having unique structural and functional characteristics, has limited the development of effective EMR-based treatments for many skin conditions.

Effectively reaching and limiting thermal damage to target structures within skin tissue by laser radiation is complicated by a variety of intrinsic and extrinsic factors. Intrinsic factors include, without limitation, the depth of the target structure within tissue and the associated absorption of light by non-targeted structures overlying the target (which may involve a plurality of intervening structures each having different light absorption and thermal characteristics), the scattering of light within the skin above the target, the TRT of the target structure and intervening non-target structures, and the removal (or non-removal) of heat by blood flowing through dermal and subdermal layers. Extrinsic factors include, also without limitation, the wavelength, pulse width, power, fluence, spot size, and other characteristics of the laser used to treat the target tissue or structure.

Acne vulgaris, more commonly referred to simply as acne, is the most common reason for office visits to dermatologists in the United States. Over 60 million Americans suffer from acne. Treatment options include topical applications such as disinfectants (e.g., benzoyl peroxide), retinoids (e.g., Retin-A), and antibiotics (e.g., clindamycin and erythromycin), as well as ingested compounds such as antibiotics (e.g., tetracycline), hormonal treatments (e.g., birth control pills), isotretinoin (Accutane, which has significant side effects), and optical treatments such as laser treatments, which have the benefit of avoiding the side effects and inconvenience of pharmaceuticals and topical treatments but which, at present, have limited effectiveness for a variety of reasons including the previously noted problems of skin tissue complexity and the limitations of existing laser systems. More recently, nanosphere particles have been deposited into skin pores and/or follicles, followed by heating of the nanoparticles with laser light to treat acne. Photodynamic therapies, in which an agent is applied to the skin to increase its sensitivity to light, have also been used in conjunction with laser or other light (e.g., blue light) to treat acne.

There is a need for improved laser systems having greater efficacy for treating acne. The present invention discloses systems and methods using lasers to achieve improved treatments for a variety of medical conditions including, without limitation, acne. In one aspect, the present disclosure provides improved pulse duration control to avoid damage to non-targeted structures and to more precisely control thermal damage to targeted structures. In one aspect, the disclosure provides systems and methods to ensure that each pulse, or a group of pulses, achieves a desired skin temperature, and does not exceed the desired temperature. This becomes highly important when the patient's skin varies in thickness or composition, such that target skin areas (e.g., spots to which one or more laser pulses are applied) may reach significantly different temperatures when the same laser pulse is applied to different skin areas. The disparity in skin temperatures for a pre-defined laser pulse for different skin areas is magnified when the target structure is deeper in the skin, because of the greater scattering and absorption of energy by overlying tissue that occurs at greater skin depths.

Heating in tissues depends upon both the absorption of the irradiated tissue structures for the wavelength of laser light used, as well as their thermal relaxation times, which is a measure of how rapidly the affected structure returns to its original temperature. By delivering the laser energy in a pulse with a time duration less than the TRT of the target tissue, highly localized heating (and destruction) of a tissue target structure (e.g., melanin, sebum, sebaceous gland, collagen) can be achieved, thereby minimizing damage to non-target structures (e.g., non-targeted skin layers, blood vessels, etc.). If the laser pulse duration is less than the TRT of the target tissue, no significant heat can escape into non-target structures, and damage to non-target structures is limited.

For deeper target structures such as sebaceous glands, which often range from 0.3-2.0 mm (more commonly 0.5-1.0 mm) below the outer surface of the epidermis, damage to overlying tissue structures is difficult to control or limit, since the laser energy must pass through those tissue structures before reaching the target tissue structures. The overlying tissue structures absorb energy depending upon their respective depths and absorption coefficients, with the result that undesired damage may frequently be done to tissue structures overlying deeper target structures. In some instances, the target structures are either sufficiently shallow, or the treatment temperature to which the target structures are raised is sufficiently low, that the heating of overlying structures may not cause excessive damage. Even where the risk of overheating the overlying structures of a relatively deep target is minimal, however, accurate temperature control of the target structure may be poor, resulting in overheating or underheating or the target structure, discomfort to the patient, or a combination of such undesired effects.

The skin surface may be cooled to limit the temperature increase (and consequent damage) to non-target overlying structures, as well as to limit discomfort and pain to the patient. However, existing systems lack precise control of the cooling process, such that achieving both a desired level of photothermal damage to deeper target structures and minimizing damage to non-target overlying structures has proven elusive. In many cases, the skin is cooled either too much—in which case the deeper target structure fails to reach a temperature damage threshold—or too little, in which case non-target overlying structures are damaged and the deeper target structure may be excessively damaged. There is a need for laser-based treatment systems having improved temperature control of the cooling process to ensure that target structures reach a desired temperature (e.g., a thermal damage temperature) and that thermal damage to non-target structures is minimized or controlled to an acceptable level.

In U.S. Pat. No. 8,474,463, a treatment system for acne vulgaris is described that uses a pulsed laser to damage sebaceous gland tissue. The system uses a laser having a wavelength in the range of 800 nm and 1200 nm, with pulses having a peak power of 10-14 kW for pulses in the range of 100-3000 μsec, a pulse repetition rate of 2-12 Hz, and a fluence of at least 8 J/cm2, typically 10-20 J/cm2. The system of the '463 patent, however, lacks the precise control of temperature necessary to achieve with consistency both a desired damage level to the target structure and avoid or limit damage to overlying structures. There is a need for dermatological laser systems that are able to efficiently treat a variety of medical conditions to achieve these goals.

SUMMARY

In one embodiment, the invention comprises a method of treating the skin of a patient with a therapeutic laser pulse, the method comprising: a) applying a contact cooling element comprising a cooling window to a first skin area of the patient; b) cooling at least a target skin area within the first skin area from a first surface temperature to a second surface temperature prior to initiating the application of a therapeutic laser pulse to the target skin area; c) initiating the application of a therapeutic laser pulse to the target skin area through the cooling window at a first timepoint; d) determining a surface temperature of the target skin area at least once during the application of the therapeutic laser pulse based on infrared energy radiated from the target skin area through the cooling window; and e) terminating the application of the therapeutic laser pulse to the target skin area at a second timepoint based at least in part on the at least one surface temperature determination.

In one embodiment, the invention provides a method of treating the skin of a patient with a therapeutic laser pulse, the method comprising: a) applying a contact cooling element comprising a cooling window to a first skin area of the patient; b) initiating the application of a therapeutic laser pulse to the target skin area through the cooling window at a first timepoint; c) determining a surface temperature of the target skin area one or more times during the application of the therapeutic laser pulse based on infrared energy radiated from the target skin area through the cooling window; d) terminating the application of the therapeutic laser pulse to the target skin area at a second timepoint based at least in part on the at least one surface temperature determination; and e) performing at least one cooling action selected from 1) cooling the target skin area from a first skin temperature to a second skin temperature using the contact cooling element prior to initiating the application of the therapeutic laser pulse to the target skin area; and 2) cooling the target skin area from a third skin temperature to a fourth skin temperature using the contact cooling element after terminating the application of the laser pulse to the target skin area.

In one embodiment, the method comprises a method of treating the skin of a patient with a therapeutic laser pulse, the method comprising: a) applying a contact cooling element comprising a cooling window to a first skin area of the patient; b) cooling at least a target skin area within the first skin area from a first surface temperature, using the contact cooling element; c) determining a surface temperature of the target skin area a plurality of times during the application of the contact cooling element to the first skin area based on infrared energy radiated from the target skin area through the cooling window prior to initiating the application of a therapeutic laser pulse to the target skin area; d) initiating the application of a therapeutic laser pulse to the target skin area through the cooling window at a first timepoint based on one or more of the plurality of surface temperature determinations of the target skin area; e) determining a surface temperature of the target skin area at least once during the application of the therapeutic laser pulse, based on infrared energy radiated from the target skin area through the cooling window; and f) terminating the application of the therapeutic laser pulse to the target skin area at a second timepoint based at least in part on the at least one surface temperature determination.

DESCRIPTION

Figure 1:
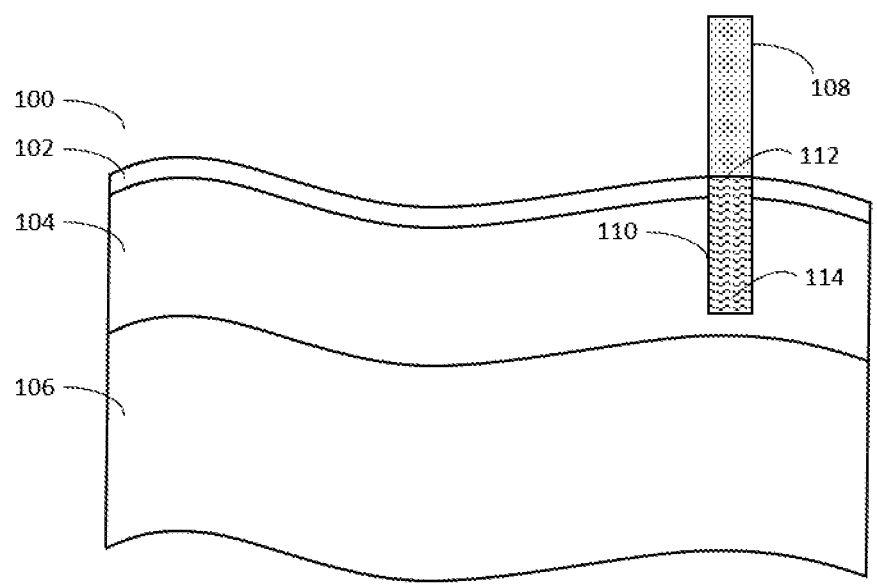
FIG. 1 is a cross-sectional illustration of skin tissue depicting the epidermis, dermis, and hypodermis, with a laser pulse applied to a portion thereof.

Exemplary embodiments of the present disclosure are illustrated in the drawings, which are illustrative rather than restrictive. No limitation on the scope of the technology, or on the claims that follow, is to be implied or inferred from the examples shown in the drawings and discussed herein.

Treatment of many dermatological conditions involve using laser light to heat a target skin area to thermally damage a selected structure within the target skin area. Laser treatment may be ablative or non-ablative, and may result in a healing response to the damaged area to improve the patient's condition. Consistently accurate delivery of energy to targeted structures to achieve a desired level of damage to a target structure, while minimizing the delivery of energy and corresponding damage to non-targeted structures, has remained an unrealized goal. The present disclosure is directed to providing systems and methods to achieve these objectives.

As used herein "target skin area" refers to the skin receiving the energy of a laser pulse. The target skin area may include the surface skin area illuminated by the laser pulse, as well as deeper structures beneath the surface skin area that receive at least a portion of the energy from the laser pulse. As such, "target skin areas" treated by a laser pulse may refer to a volume of skin as opposed to a true area of an outer surface of the epidermis.

As used herein, "surface temperature" in reference to a target skin area refers to the temperature of the target skin area as determined or measured at or above the surface of the skin. In particular, where infrared energy radiated from a target skin area is used to measure the temperature of the skin surface, the surface temperature determination includes energy radiated from deeper in the epidermis in addition to the outermost layer of cells. Without being bound by theory, the strong scattering effects of infrared wavelengths within the epidermis limit the energy emitted and detected to the upper 100 microns, and primarily the upper portions thereof. Consequently, "determining a surface temperature" based on detection of radiated infrared energy refers to the determination of a composite or average temperature of the upper portions (e.g., tens of microns in depth) of the epidermis, and not merely the outermost layer of skin cells. In embodiments of the present invention, it provides a reliable and precise determination of the temperature of the uppermost portion of the epidermis.

In one aspect, the present invention comprises systems and methods for improved temperature control of a target skin area during the delivery of one or more laser pulses in the treatment of a medical condition. In some embodiments, the present invention comprises systems and methods for control of a surface temperature of a target skin area of a patient during a laser pulse in the treatment of a dermatological condition. In some embodiments, the present invention provides improved temperature control of a target non-surface (i.e., deeper) structure in a target skin area of a patient during a laser pulse. By providing accurate temperature control of a target skin area during the delivery of laser pulses, the invention provides systems and methods with improved efficacy, safety and/or comfort to patients being treated for a range of dermatological conditions.

In one aspect, the invention provides systems and methods of controlling a temperature of a target skin area during a laser pulse to avoid overheating the target area. Such systems allow laser treatments that avoid excessive damage to a target structure within the target skin area, and/or undesired damage to overlying non-targeted structures. In one aspect, the invention provides systems and methods of controlling a temperature of a target skin area during a laser pulse to avoid underheating a target structure, resulting in too little damage to the target structure.

In one aspect, the present invention discloses systems and methods for minimizing the temperature increase of non-target structures overlying a target structure within a target skin area during the delivery of a laser treatment to raise the target structure from a first temperature to a second temperature, such as a damage threshold temperature for the target structure. In one embodiment, the laser treatment comprises a single pulse, and the temperature of the target skin area is measured one or more times during the delivery of the pulse.

In one embodiment, the laser treatment comprises a plurality of pulses made during a single heating episode of the target skin area, and the temperature of the target skin area is determined one or more times during the single heating episode. As used herein, a "single heating episode" involves a plurality of pulses where the first pulse raises the temperature of the target skin area from a first or baseline temperature immediately prior to the first pulse, and each successive pulse in the heating episode is applied before the target skin area returns to the first or baseline temperature. Where a plurality of pulses are used to heat the target skin area to a desired temperature in a single heating episode (e.g., a damage threshold temperature for a target structure), the temperature of the target skin area may be determined during a pulse, between pulses, or a combination of during and between pulses of the single heating episode.

In one aspect, the invention comprises a method of determining the length of a laser treatment pulse based on determining the surface temperature of a target skin area one or more times during the delivery of the laser treatment pulse. By determining the surface temperature of the target treatment area during the delivery of the laser treatment pulse, the laser pulse may be terminated when the skin reaches a desired temperature that avoids overheating the target skin area and causing excessive damage to non-targeted structures, as well as terminating the pulse too early, with too little damage to the target structure(s). In some embodiments, the invention may also include skin cooling (e.g., contact cooling applied to the skin surface) to enable heating of deeper structures (such as a sebaceous gland or the root of a hair follicle in the dermis) to a damage threshold temperature while minimizing the heat delivered to overlying non-targeted tissue structures.

In one aspect, the invention comprises a method of determining the duration of a laser treatment comprising a plurality of laser pulses in a single heating episode of a target skin area from a first surface temperature to a second surface temperature. The duration of the laser treatment is based on determining the surface temperature of the target skin area a plurality of times during the delivery of the plurality of laser treatment pulses.

As used in connection with temperature determinations, "real-time" refers to temperature determinations (e.g., temperature measurements or calculations based on data from a temperature sensor) performed during an action (e.g., during the cooling of a target skin area or during the delivery of a laser pulse to a target skin area) and used by a processor to determine a timepoint for terminating the action or initiating the performance of another action. In one aspect, the invention comprises real-time temperature determinations during the cooling of a first skin area, and the temperature determinations may be used to perform an action such as terminating the cooling process, initiating the delivery of a laser pulse to a target skin area within the first skin area being cooled, or terminating the delivery of a laser pulse to a target skin area within the first skin area being cooled. In another aspect, the invention comprises real-time temperature determinations during the delivery of a laser pulse to a target skin area without cooling, and using the temperature determinations as a basis for terminating the delivery of the laser pulse to a target skin area.

In one aspect, the invention comprises real-time temperature determinations performed during the delivery of a therapeutic laser pulse (or during or between pulses delivered as a plurality of pulses comprising a single heating episode), which may be used (e.g., by a processor executing a treatment algorithm) to perform an action such as terminating the delivery of a laser pulse, initiating the delivery of one of a plurality of pulses comprising a single heating episode, adjusting a parameter of a therapeutic laser pulse, or initiating, terminating, or adjusting (e.g., increasing the rate of) a cooling process associated with the delivery of therapeutic laser pulse(s).

In one aspect, the invention comprises a method of treating a patient having hyperhidrosis (i.e., excessive sweating) by controlled heating of a target skin area from a first surface temperature to a second surface temperature, where the second surface temperature corresponds to a temperature resulting in thermal damage to a sweat gland within the target skin area. In one embodiment, the duration of the laser treatment pulse is based on determining the surface temperature of the target skin area a plurality of times during the delivery of the laser treatment pulse. In one embodiment, the laser treatment pulse is terminated when the second surface temperature reaches a value indicative of the deeper sweat gland reaching a sweat gland treatment temperature. The second surface temperature corresponding to the sweat gland reaching the sweat gland treatment temperature may be identified prior to treatment, e.g., by thermal (mathematical) modeling of the heating of the target skin area based on the parameters of the treatment laser such as wavelength, energy flux, and thermal characteristics of the target skin area such as thermal conductivity, the absorption coefficients of various tissue structures and/or chromophores, etc.

In one aspect, the invention comprises a method of treating a patient having acne vulgaris by controlled heating of a target skin area from a first surface temperature to a second surface temperature, where the second surface temperature corresponds to a temperature resulting in thermal damage to a sebaceous gland within the target skin area. In one embodiment, the duration of the laser treatment pulse is based on determining the surface temperature of the target skin area a plurality of times during the delivery of the laser treatment pulse. In one embodiment, the laser treatment pulse is terminated when the second surface temperature reaches a value indicative of the deeper sebaceous gland reaching a sebaceous gland treatment temperature. The second surface temperature corresponding to the sebaceous gland reaching the sebaceous gland treatment temperature may be identified by thermal modeling as previously discussed.

FIG. 1 is a side view illustrating a cross-sectional view of a portion 100 of the skin of a patient, including the outermost epidermis 102, the middle layer or dermis 104, and the bottom layer or hypodermis 106. The epidermis 102 has a thickness of about 80-100 μm, which may vary from patient to patient, and even for a single patient depending upon age, health status, and other factors. It includes up to five sub-layers (not shown) and acts as an outer barrier.

The dermis 104 has a thickness of about 1-5 mm (1000-5000 μm). It contains the blood vessels, nerves, hair follicles, collagen and sweat glands within the skin. Because skin conditions frequently involve structures in the dermis, many laser systems must include sufficient energy to penetrate into the dermis to reach and treat structures therein. Careful selection of a number of parameters must be made in the design and construction of laser systems for treatment of a variety of skin conditions to achieve a desired level of damage to a target structure while minimizing or avoiding damage to non-targeted (e.g., overlying) structures. For example, incorrect selection of the laser wavelength, pulse width, energy per pulse, the use (or nonuse) of a seed laser, or the pump energy of the laser source or amplifier may result in undesired damage as well as poor performance in treating a dermal structure of interest. Numerous other system choices, such as the use or non-use of an articulating arm for delivery of the laser light to a handpiece for application to the patient's skin, may also affect overall system performance.

The lowest layer of the skin is the hypodermis 106, which includes adipose tissue and collagen. The hypodermis 106 helps control body temperature by insulating the structures of the body below the skin. In addition, the hypodermis protects the inner body tissues from damage by absorbing shock and impacts from outside the body. Because the hypodermis contains fat, its thickness varies widely from person to person based on diet, genetic makeup, and other factors.

FIG. 1 depicts a laser beam 108 applied to a target skin area 110 of the skin 100. The target skin area 110 comprises a surface skin area 112, as well as underlying skin tissue 114 that absorbs at least a portion of the energy of the laser beam 108.

Figure 2:
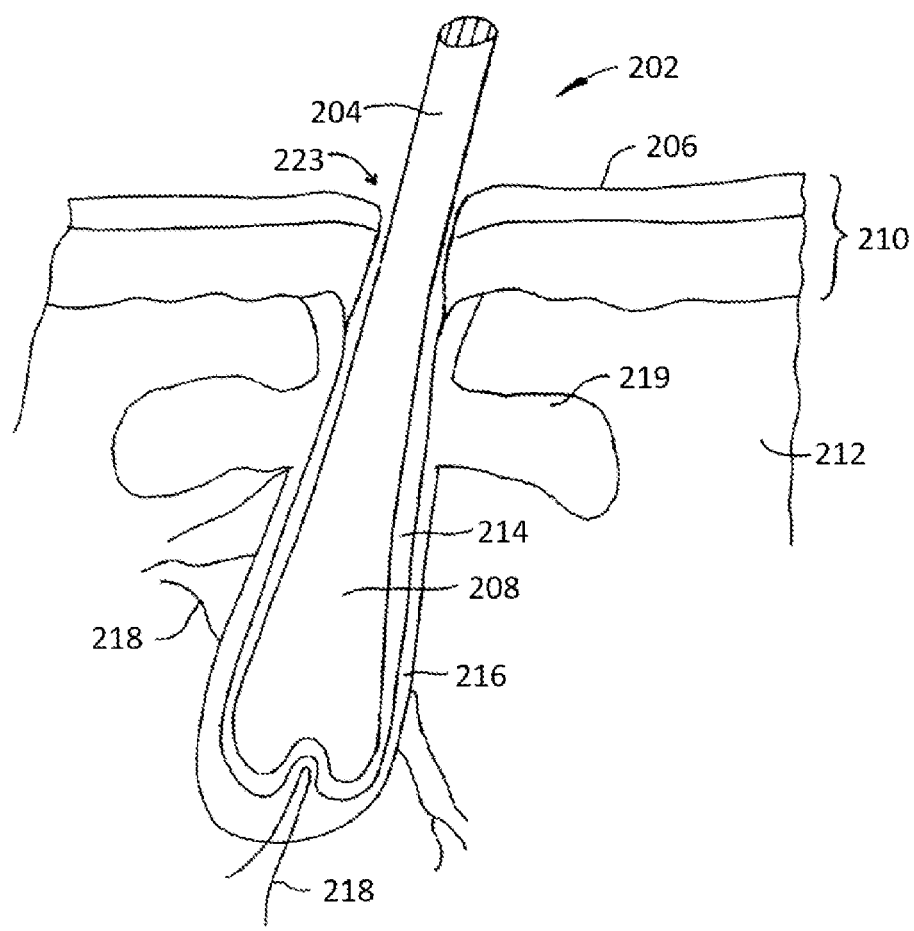
FIG. 2 is a cross-sectional illustration of skin tissue depicting a hair follicle and a sebaceous gland.

FIG. 2 is a side view of the skin of a patient illustrating in simplified form, a hair 202 including a hair shaft 204 extending beyond the exterior skin surface 206. Hair shaft 204 includes a root 208 located below epidermis 210 in the dermis 212. The base, or papilla, of root 208 is located about 4 mm below exterior skin surface 206. Root 208 is housed within hair follicle 214 and is surrounded by tissues including connective tissue sheath 216 and blood vessels 218. Follicle 214 includes a sebaceous gland 219 below an opening 223. Sebaceous glands such as gland 219 are typically located at depths ranging from about 0.3 mm (300 μm) to about 2.0 mm (2000 μm) below exterior skin surface 206, but their depth varies depending upon body location.

Epidermis 210 includes melanin (not shown), a dark pigment found in tissues of the hair, skin and eyes. Melanin, the primary determinant of skin color, is located within globular structures known as melanosomes, which are produced by skin cells called melanocytes. Darker skin has more melanosomes (and thus more melanin) per unit skin area compared to lighter skin. Laser systems targeting deeper structures such as sebaceous gland 219 in the dermis may present a higher risk of patient discomfort where wavelengths having a relatively high absorption coefficient in melanin are used. Without being bound by theory, when laser light at wavelengths readily absorbed by melanin is applied to dark skin (or dark tattoos having ink particles that absorb laser light at similar wavelengths to melanin), the energy absorbed by the melanin (or tattoo ink particles) attenuates part of the laser energy that otherwise would reach deeper structures absent the melanin or ink particles, heating the skin of the epidermis and/or upper dermis to a greater degree than lighter/un-tattooed skin. Additional energy—either by providing higher fluences, higher energy per pulse, or longer treatment times—must be applied to reach deeper structures to heat them to a target treatment temperature. However, higher pulse fluences and pulse energy may compound the problem, since the additional energy delivered in a shorter time period will cause the skin temperature to rise even faster than using lower fluences or energies. In addition, longer treatment times can only deliver more energy to the target if the energy is delivered within the TRT of the target tissue—otherwise, the additional energy largely leaks from the target tissue into adjacent non-target tissue.

Accordingly, in one aspect, the present invention provides laser treatment systems to minimize discomfort by adjusting one or more parameters based on the skin type of the patient. In one embodiment, the invention provides systems and methods for determining a skin type of a patient and automatically adjusting one or more treatment parameters based on the skin type of the patient. This may involve, for patients having darker skin types, one or more of: providing additional cooling of the patient's skin prior to applying a laser therapy to the patient's skin; lowering a first skin temperature at which a therapy pulse is initiated and applied to the patient's skin; lowering a fluence of a laser therapy; lowering a peak power of the laser pulses of a laser therapy; providing a longer pulse width of a pulsed laser therapy; and providing a larger beam diameter for a pulsed laser therapy.

Successful treatment of acne involves damaging sebocytes and/or sebaceous glands. This involves heating sebum, which produced by and located within the sebaceous glands, to damage the gland. Accordingly, it is desirable to select a wavelength of light that is highly absorbed by sebum, preferably more so than competing skin chromophores (e.g., water), to limit the damage to non-targeted tissue and concentrate the laser energy delivered into the targeted sebaceous gland to the exclusion of non-targeted tissues and structures. In addition, because sebaceous glands are relatively deep structures located in the dermis at depths of 300-2000 μm (0.3-2.0 mm), it is desirable to select a wavelength of light capable of non-ablative penetration to these depths.

Figure 3A:
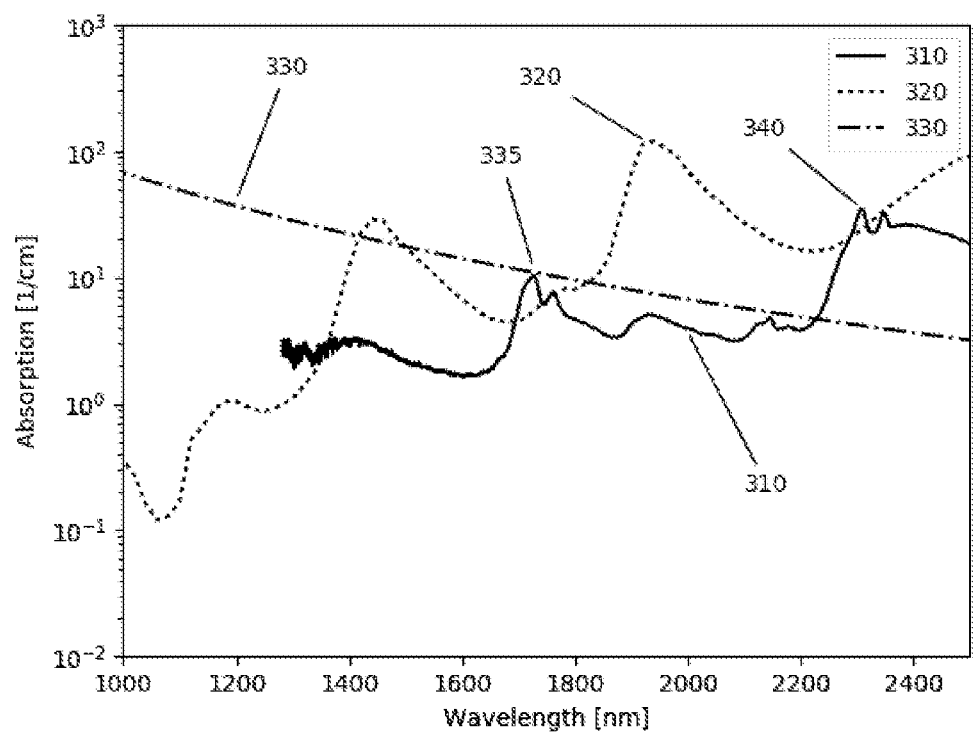
FIGS. 3A and 3B are graphs illustrating the absorption coefficients of human sebum lipid, water, and melanosomes for various wavelengths of light.
Figure 3B:
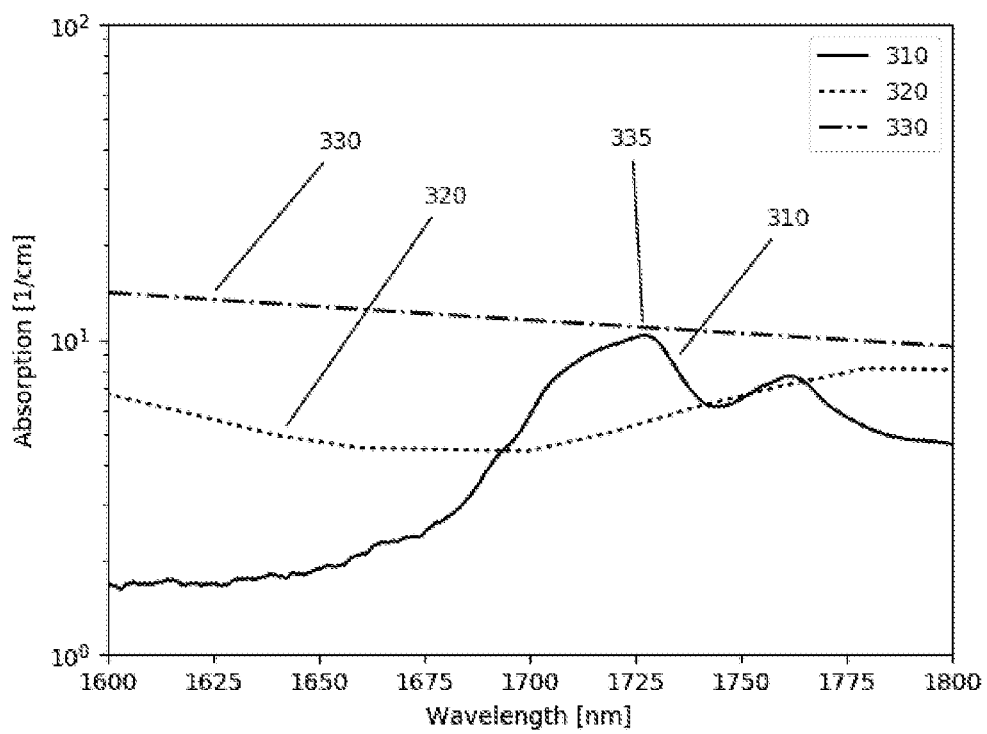

FIGS. 3A and 3B are graphs illustrating the absorption curves for several chromophores of interest (water, sebum, and melanosomes) at wavelengths of light for portions of the near-infrared spectrum (about 750 nm-1400 nm) and the short-wavelength infrared spectrum (about 1400-3000 nm). FIG. 3A illustrates the absorption curve 310 for sebum, the water absorption curve 320, and the absorption curve 330 for melanosomes. It will be appreciated that in laser treatment systems directed toward other conditions, e.g., tattoo removal or pigmented lesions, the absorption of other structures or chromophores (e.g., inks of various colors, hemoglobin, etc.) will be important considerations in selecting laser treatment system parameters such as wavelength, fluence, peak power, etc.

FIG. 3A demonstrates that the sebum absorption curve 310 has a peak at about 1727.5 nm, meaning that sebum absorbs laser light at this wavelength more strongly than light at other nearby wavelengths, e.g., 1650 nm or 1800 nm. The absorption coefficient of water is less than that of sebum in a range of from about 1693 nm to about 1742 nm, and within a range of from about 2280-2360 nm. The absorption coefficient of melanosomes exceeds that of sebum at all wavelengths less than about 2225 nm, although only by a small amount at the 1727.5 nm peak for sebum, as demonstrated at point 335 of FIG. 3A, where the two absorptions curves approach one another. It will be appreciated by persons of skill in the art that the concentration of sebum, water, and melanin may vary from patient to patient for a given area, and even within a particular patient depending upon the target tissue structure(s), the hydration status of the patient, and the skin type or area of the patient.

As shown more clearly in FIG. 3B, the absorption coefficient for sebum at a peak of about 1727.5 nm is approximately twice that of water, and is only slightly less than that of melanosomes. Specifically, the absorption coefficient for melanosomes at 1727.5 is about 11.0 cm-1, and that of sebum is about 10.3 cm-1. Accordingly, in one embodiment, the invention comprises a laser providing pulsed laser light at a wavelength of between 1693-1742 nm, more preferably at about 1720-1730 nm, and more preferably still at about 1727.5 nm.

Referring again to FIG. 3A, sebum has a further absorption peak (340) of about 2305 nm, exceeding that of both water and melanosomes at the same wavelength. Accordingly, in one embodiment, the invention comprises a laser providing pulsed laser light at a wavelength of between about 2287-2318 nm. Although sebum strongly absorbs light at 2305 nm, light at this wavelength is less suitable than light at 1727.5 nm because its penetration depth into skin is much less than that of light at 1727.5 nm. In general, at wavelengths shown in FIGS. 3A and 3B, the penetration of light decreases with increasing wavelength. Accordingly, treatment of acne and other conditions with laser light involves multiple tradeoffs, including the relative absorption coefficients of target and non-target tissues/structures, penetration depth of the wavelength of interest into skin, laser power, laser pulse fluence, pulse duration, pulse frequency, etc.

Figure 4A:
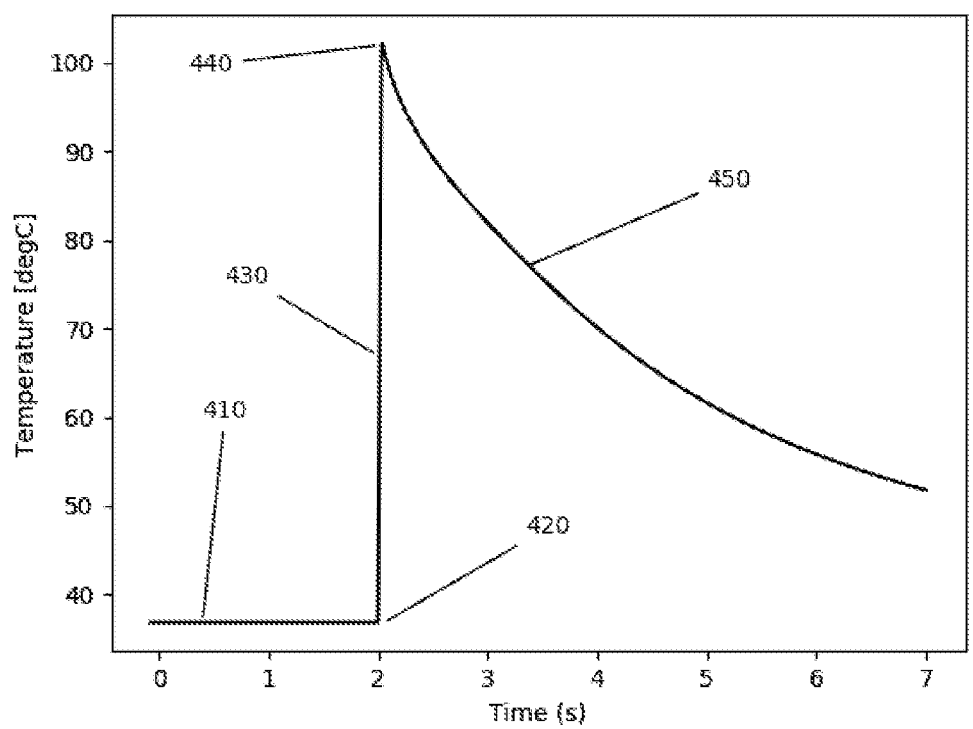
FIG. 4A is a graph illustrating a surface temperature profile of a target skin area according to a mathematical model of a treatment with a laser pulse.
Figure 4B:
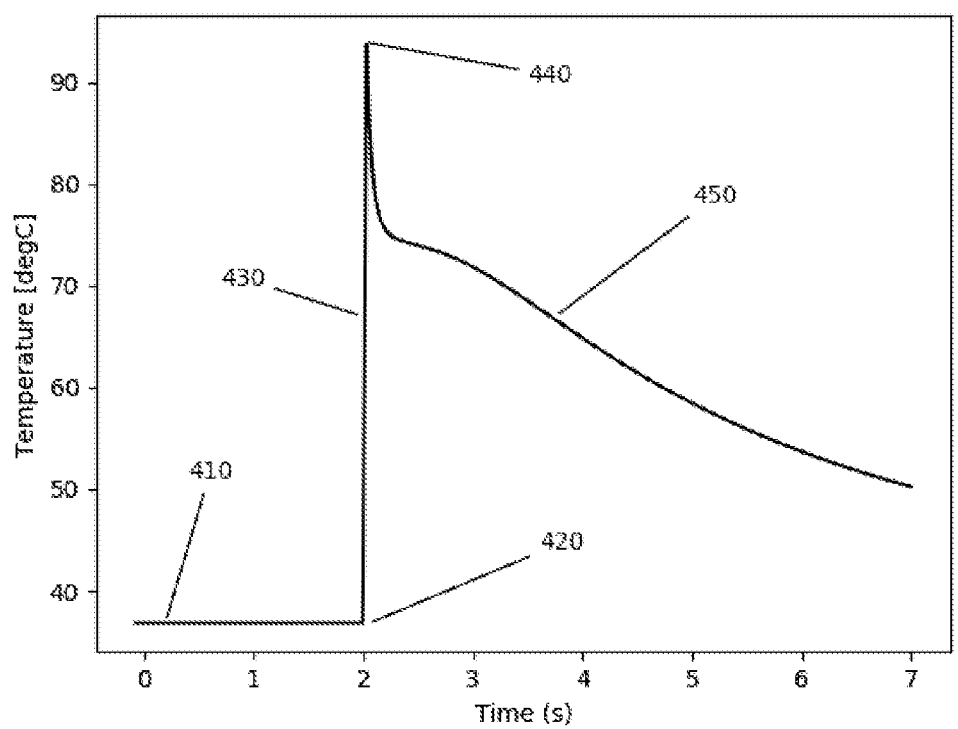
FIG. 4B is a graph illustrating a sebaceous gland temperature profile within a target skin area according to the mathematical model of the laser pulse of FIG. 4A.

FIGS. 4A and 4B illustrate exemplary temperature profiles of the surface of a target skin area (FIG. 4A) and a sebaceous gland located below the surface of the target skin area (FIG. 4B) during a laser pulse according to a mathematical model of one embodiment of the present invention. The laser pulse is intended to raise the temperature of the sebaceous gland to a temperature that will result in a desired cell population death for sebocytes receiving energy from the laser pulse. In this embodiment, the laser pulse is a tophat pulse (i.e., having a uniform intensity profile over the covered area) used to heat a target skin area and has a wavelength of 1727.5 nm, a pulse duration of 30 msec, a beam diameter of 2.8 mm, a power of 75 W, a pulse energy of 2.25 J, and a fluence of 37 J/cm2. For purposes of illustration, the skin is depicted as remaining at body temperature for 2 seconds prior to the application of the pulse, although it will be appreciated that the initial time period before pulse initiation could be shown as any time period.

Referring to FIG. 4A, at time t=2 seconds, a single pulse of laser light having the parameters noted above is initiated and applied to a target skin area, depicted at point 420. The surface temperature of the skin rises during the pulse, as shown by line 430, to slightly above 100° C. as shown by peak 440. After the pulse is terminated, the skin surface temperature of the target area cools rapidly over the next several seconds, as indicated by curve 450, falling to below 60° C. within 4 seconds (t=6 seconds) after the termination of the pulse.

FIG. 4B illustrates the temperature profile of a sebaceous gland located at a depth of 650 μm below the skin surface in the laser pulse model of FIG. 4A. As in FIG. 4A, the skin remains at body temperature for 2 seconds (410) prior to the initiation of a single pulse (421) applied to the target skin area. The temperature of the gland rises during the pulse (430) to a maximum temperature 440 of about 92° C.—less than the temperature of the skin surface illustrated in FIG. 4A due to scattering and the energy absorbed by the tissue overlying the sebaceous gland. However, because the pulse wavelength of 1727.5 nm is preferentially absorbed by the sebaceous gland (as discussed in connection with FIGS. 3A and 3B), comparatively more energy from the laser pulse that reaches the gland is absorbed by the oily tissue therein compared to overlying tissue containing higher water content. Consequently, the temperature profile (450) of the sebaceous gland after termination of the pulse at 440 differs significantly from that of the skin surface temperature depicted in FIG. 4A. Although the temperature initially falls rapidly to about 85° C., the temperature thereafter falls more slowly than the surface temperature shown in FIG. 4A.

The pulse in FIGS. 4A and 4B has energy levels below those necessary to ablate skin tissue. Although this pulse will result in thermal damage to the sebaceous gland and could be used to treat acne, temperatures above 45-50° C. are likely to result in significant discomfort when they persist, as illustrated in FIG. 4A, for 4 seconds or longer. Accordingly, the pulse depicted in FIG. 4A would have limited application as a viable treatment to most patients. In one embodiment, the laser pulses described in connection with FIGS. 4A and 4B result in temperatures too high to be used for treatment, although they could be modified (e.g., by lowering pulse fluences, shortening pulse treatment times, etc.) to result in skin temperatures that may be used for treatment. In one embodiment, temperatures may be lowered by skin cooling, as described in connection with FIGS. 5A and 5B.

Figure 5A:
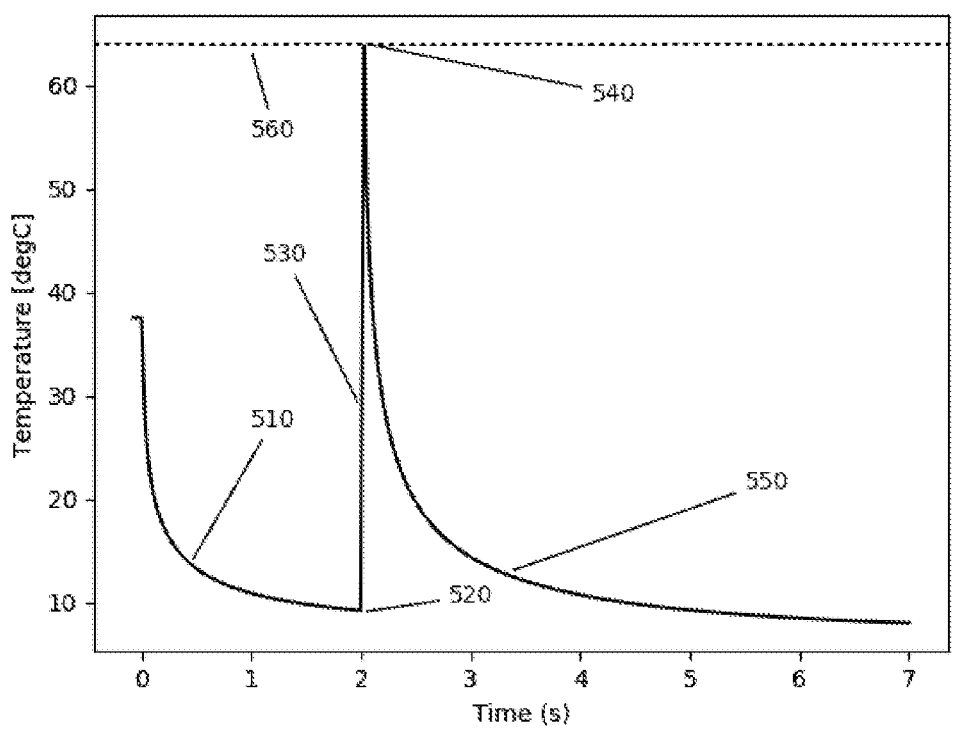
FIG. 5A is a graph illustrating a surface temperature profile of a target skin area before, during, and after a laser pulse treatment with skin cooling, according to a mathematical model.
Figure 5B:
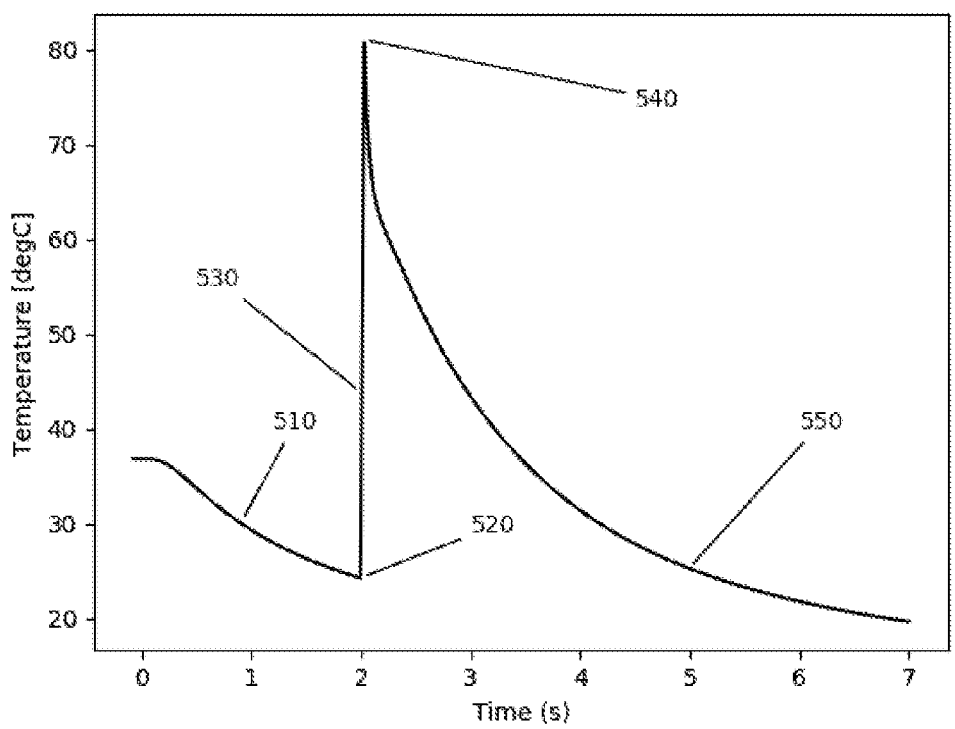
FIG. 5B is a graph illustrating a sebaceous gland temperature profile within a target skin area before, during, and after a laser pulse treatment with skin cooling, according to the mathematical model of FIG. 5A.

FIGS. 5A and 5B illustrate exemplary temperature profiles of portions of a target skin area during a laser pulse according to a mathematical model of another embodiment of the present invention. In the embodiment of FIGS. 5A and 5B, the laser pulse has the same parameters as those of FIGS. 4A and 4B (wavelength λ=1727.5 nm; pulse duration=30 msec; beam diameter=2.8 mm, power=75 W; pulse energy=2.25 J; fluence=37 J/cm2). However, in contrast to the embodiment of FIGS. 4A and 4B, in FIGS. 5A and 5B the target skin area is cooled prior to, during, and after the application of the laser pulse.

Although persons of skill in the art will appreciate that many known methods and modes of precooling the skin may be used, the embodiment of FIGS. 5A and 5B are modeled on a system having a contact cooling element that is applied to a first skin area that includes a target skin area to be treated by the laser pulse. The contact cooling element includes a cooling window that, in some embodiments, directly contacts the first skin area, and the target skin area actually irradiated by the laser pulse is wholly located within the first skin area. Although a variety of materials may be used as the contact cooling window, in the embodiment of FIGS. 5A and 5B, the cooling system includes a sapphire cooling window cooled by a thermoelectrical cooler (TEC). The sapphire cooling window has a thickness of 3 mm and a diameter of 1 inch (25.4 mm), although many different sizes, shapes, thicknesses, and materials may be used in cooling window embodiments disclosed herein. For example, although the cooling window modeled in the embodiment of FIGS. 5A and 5B was circular, other cooling window shapes such as square, rectangular, or other polygonal or nonpolygonal shapes could be used in different embodiments and for different tissue types. The cooling window was modeled as being cooled to a temperature of 5° C.

In alternative embodiments, non-contact cooling systems (e.g., cold air or other fluid circulated onto or across the surface of a target skin area) may be used to cool the skin. Without being bound by theory, it is believed that the thermal resistivity of the skin and the thermal coupling between the skin and gases such as air typically preclude non-contact systems from providing adequate cooling capacity during the delivery of laser pulses to both effectively treat deeper target structures and prevent the skin surface from reaching temperatures likely to result in significant discomfort. Accordingly, contact cooling systems are preferred cooling systems. In still other embodiments, evaporative cooling systems (e.g., sprayed coolant evaporating from the skin) may be used.

Referring to FIG. 5A, the contact cooling element at 5° C. is applied to the skin at time t=0, and the temperature falls rapidly along curve 510 to a target temperature of about 10° C. at time t=2 second, at which point (520) the laser pulse is applied to the skin. Delivery of the laser pulse to the target skin area is continued until a target surface temperature 560 of the target skin area is reached at point 540, at which point the laser pulse is terminated. Because the contact cooling element continues to cool the skin by direct contact both during and after the laser pulse, the surface temperature of the target skin area falls rapidly along curve 550 after the laser pulse is terminated.

FIG. 5B illustrates the temperature profile of a sebaceous gland located at a depth of 650 µm below the skin surface in the cooling and laser pulse delivery process of FIG. 5A. When the contact cooling element is applied to the skin at time t=0, the temperature of the gland declines as shown by curve 510, but much less rapidly than the temperature decline of the skin surface, depicted in FIG. 5A. The laser pulse is initiated at point 520, and the temperature of the gland rises along line 530 until the laser pulse is terminated at point 540. The gland temperature thereafter falls along line 550, but the curve is noticeably less steep (i.e., the temperature fall is less rapid) than the surface temperature decline following the pulse termination.

Because direct measurement of the gland temperature is difficult or impossible given its depth within the skin, in embodiments of the present invention, surface skin temperature may be monitored as an indirect indication of the gland temperature. It should also be noted that, because the goal of the laser treatment process is to heat the sebaceous gland to a damage threshold temperature, the cooling of the gland (as opposed to the skin surface) shown by curve 510 in FIG. 5B is undesired, but is tolerated as an unavoidable consequence of the protective precooling of the overlying skin tissue. By precooling the overlying skin tissue to a desired surface temperature of about 10° C. as shown in FIG. 5A, a downward cooling wave is generated in the target skin area, propagating from the skin surface toward the deeper tissues in the dermis and hypodermis. This precooling process may be controlled such that, for a sebaceous gland within a known depth range, when the laser pulse is delivered to heat the target skin area, the protectively cooled overlying skin remains below a damage threshold temperature while the target sebaceous gland reaches a damage threshold temperature. This is facilitated by selecting a laser wavelength for which the absorption coefficient of sebum and/or sebaceous gland tissue exceeds that of water, the primary chromophore of most of the overlying dermal and epidermal tissue.

Comparing FIGS. 5A and 5B, the precooling process allows the sebaceous gland to reach a temperature of about 78° C. at the termination of the laser pulse—about 13° C. above that of the target skin area at the surface (about 62° C.) at pulse termination. Although the overlying tissue is unavoidably heated during the laser pulse delivery, careful precooling of the overlying tissue to a desired temperature before initiating the laser pulse allows the surface temperature to be precooled to a temperature well below that of the sebaceous gland when the laser pulse is initiated (about 10° C. for the skin surface vs. about 22° C. for the sebaceous gland as shown by FIGS. 5A and 5B at point 520). This temperature difference occurs because the cooling window causes a thermal gradient between the skin surface and deeper structures as heat is removed through the window. In addition, the pulse wavelength (1727.5 nm) is more highly absorbed by the sebaceous gland than the non-target overlying tissue structures. As a result, the non-targeted tissue overlying the sebaceous gland is heated by the laser pulse to a lower temperature (about 63° C. as shown in FIG. 5A at point 540) than the targeted sebaceous gland (about 81° C. as shown in FIG. 5B at point 540), thereby minimizing not only damage to the non-targeted tissue but patient discomfort as well.

Figure 5C:
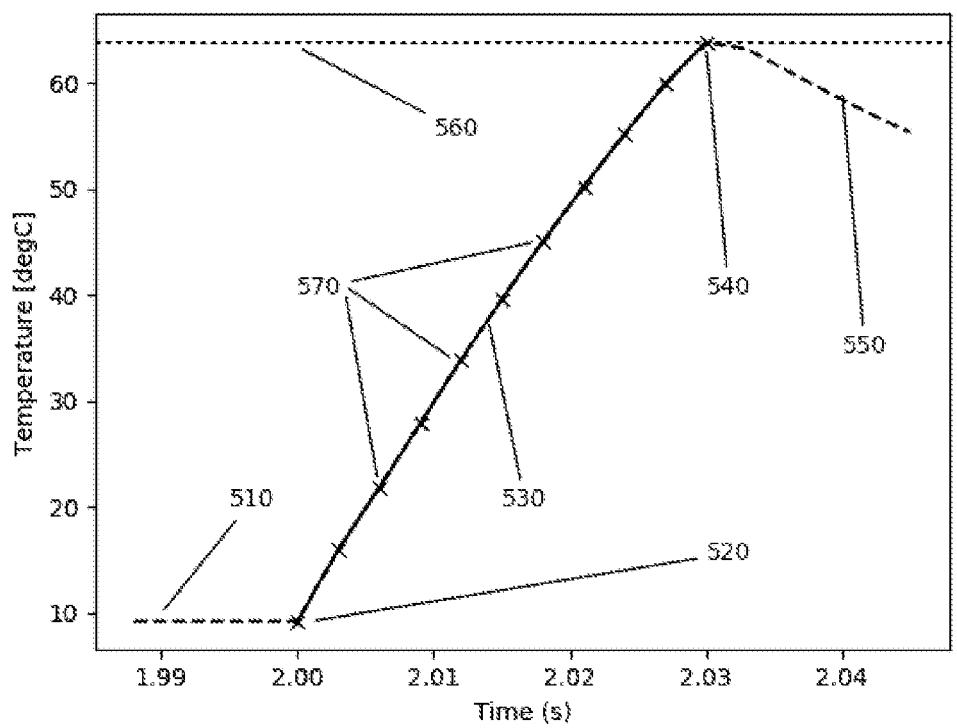
FIG. 5C is more detailed graph illustrating a surface temperature profile for a target skin area during treatment with a laser pulse according to the mathematical model of FIG. 5A.

Certain systems and methods of the present invention are facilitated by a method of controlling the duration of a pulse to limit the surface temperature of a target skin area to a desired threshold. FIG. 5C demonstrates a method of achieving such control by monitoring the temperature of a pulse during the delivery of the pulse. The surface temperature of the skin may be determined one or more times during pulse delivery, and the pulse may be terminated based on one or more of the skin temperatures thus determined. In one embodiment consistent with the skin cooling system used in FIGS. 5A and 5B, the skin temperature is periodically determined during the pulse delivery, and the pulse is terminated when the surface skin temperature reaches (or is within a desired interval of) a threshold temperature.

FIG. 5C, illustrates a more precise temperature profile of the delivery of the pulse of FIGS. 5A and 5B. From time t=1.99 to t=2.00 seconds, the temperature of the skin near the surface (modeled in FIG. 5C at a depth of 100 µm) is relatively constant at about 10° C., as indicated by line 510. At time t=2.00 seconds (520), the pulse is initiated and applied to the skin through the sapphire cooling window. Simultaneously, the first of a plurality of surface temperature determinations of the target skin area 570 is made. Pulse delivery continues along line 530, and the surface temperature rises until the pulse is terminated at 540. After pulse termination, the surface temperature falls as indicated by line 550. During pulse delivery, multiple temperature determinations 570 are made at equal intervals, although it will be appreciated that the frequency of temperature sampling may vary based on a variety of factors such as the time frame desired for heating the tissue, thermal relaxation of the target structure, pulse fluence, pulse power, pulse wavelength, and exogenous factors such as the damage threshold for the particular target structure (e.g., a sebaceous gland, hemoglobin, melanin, etc.), and other factors. Temperature determinations may be performed at a desired sampling interval, e.g., 100 msec or less (i.e., performing 10 or more temperature determinations per second). Depending upon the sensing element and processor used, the surface temperature of the skin may be determined at a sampling interval or time between temperature determinations of 0.001-100.0 msec (i.e., 1-100,000 µsec, or performing 10 to 1 million temperature determinations per second).

In the embodiment of FIG. 5C, the skin temperature determinations are made by sensing infrared radiation radiated from the surface of the target skin area to which the pulse is applied, although other known methods of determining or measuring a surface temperature at a particular skin location may be used. Although FIG. 5C depicts temperature measurements made at a constant interval, sampling may also be performed at non-constant intervals, e.g., varying based on the difference between a measured temperature and a desired threshold, or on other exogenous factors such as the operating speed of the sensor or processor. In one embodiment, the temperature sampling interval is increased as the surface skin temperature approaches a threshold temperature.

In one embodiment, the laser pulse may be terminated after the first temperature determination that is at or above the temperature threshold. In another embodiment, the laser pulse may be terminated based on a predicted timepoint at which the skin surface will reach the threshold temperature, without requiring that the temperature be reached or exceeded. For example, periodic predictions of when the threshold temperature will be reached may be made, e.g., by fitting a straight line or polynomial function to the temperature data each time a subsequent temperature determination is made during pulse delivery, and projecting the function forward to determine a predicted timepoint when the temperature threshold will be reached. In such embodiments, after a predetermined number of measurements have been made (or after a plurality of predictions each result in a predicted timepoint for reaching the desired temperature that are within a predetermined interval of one another), the pulse may be terminated at the predicted timepoint, and no actual temperature determination at or above the threshold may be necessary.

FIGS. 5A and 5B illustrate methods of treating a sebaceous gland according to one embodiment of the present invention. It will be appreciated, however, that embodiments of the present invention may be used to treat other structures in the dermis or hypodermis (e.g., sweat glands, hair follicles, etc.) by facilitating precise control of surface and deeper temperatures within a target skin area.

Figure 6A:
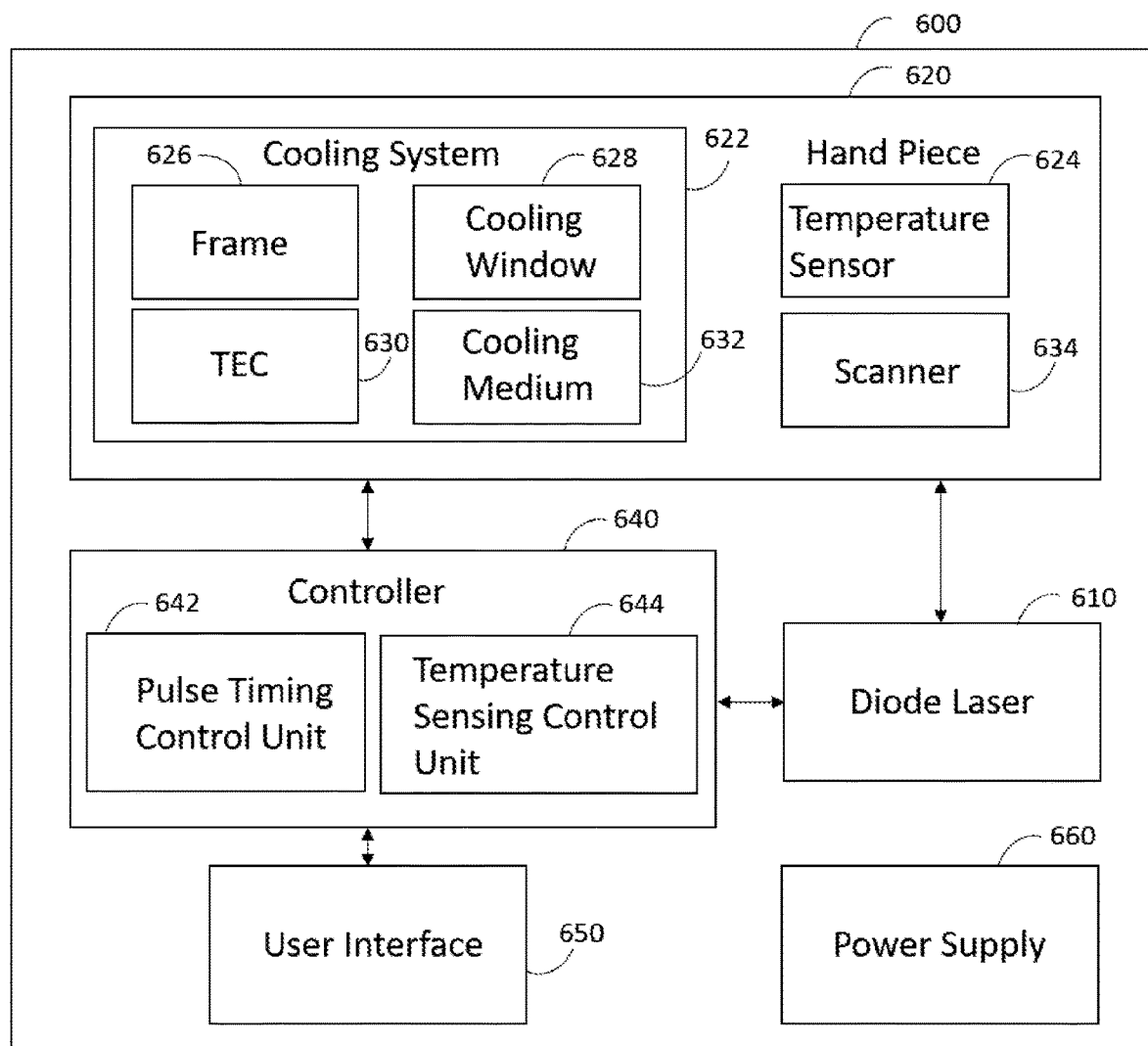
FIGS. 6A and 6B are block diagrams of embodiments of a dermatological treatment system according to the present invention.

FIG. 6A is a schematic illustration, in block diagram form, of an embodiment of a therapeutic laser system 600 for providing therapeutic laser pulses as described in connection with FIGS. 5A-C. A diode laser 610 provides a laser having a wavelength with a high absorption coefficient in a target tissue. In the embodiment of FIG. 6A, the target tissue is sebaceous gland tissue, although in the treatment of different dermatological conditions, the target tissue may be different. Diode laser 610 is optically coupled, e.g., by an optical fiber, articulating arm, or other optical coupling elements known in the art, to a handpiece 620 for delivery of a laser pulse to a target skin area to be treated. Although some systems of the present invention are described in connection with diode lasers, it will be appreciated that other laser types (e.g., fiber lasers, dye lasers, etc.) may also be used in different embodiments.

Handpiece 620 includes a cooling system 622 for cooling a first skin area that includes a target skin area within the first skin area. Cooling system 622 includes a contact cooling element comprising a cooling window 628 maintained in a fixed position in contact with a heatsink portion of a thermoelectric cooler (TEC) 630 by a window frame 626. Cooling window 628 may comprise any of a variety of IR-transmissive materials, including sapphire, ZnS, diamond, ZnSe, and other thermally conductive material that are transmissive to infrared light. In alternative embodiments (not shown), the contact cooling element may comprise components or structures in addition to cooling window 628, such as a copper (or other material having a high thermal conductivity) cooling element that is not light-transmissive to provide additional cooling capacity.

TEC 630 may be a Peltier-type cooler and has a warm side and a cold side (not shown). The heatsink portion of the TEC 630 is part of the cold side and is used to remove heat from the cooling window 628 to maintain the cooling window at desired temperature as it contacts the first skin area. A cooling medium 632 removes heat from the hot side of the TEC 630 to prevent heat buildup in handpiece 620. In one embodiment, the cooling medium comprises circulating cold water, although other thermally conductive fluids or other materials may be used in different embodiments.

To ensure efficient skin cooling, it is necessary to maintain good contact between the skin and the cooling window 628 during treatment. In one embodiment (not shown), the invention comprises one or more contact sensing elements to detect when the cooling window 628 is properly in contact with the first skin area. The contact sensing element(s) may be coupled to, or separate from, cooling window 628 and/or frame 626, and may comprise, e.g., one or more electrical contacts capable of sensing electrical activity, conductivity, or resistance of the skin indicative of adequate skin/cooling window contact. Other contact sensing elements (e.g., ultrasonic sensors) detecting different skin parameters or features associated with proper contact (e.g., force, vibration, pressure, temperature, the presence of sweat or skin oils) may also be used.

One or more skin contact indicators (not shown) may alert a user to the contact status between the skin and cooling window 628. The skin contact indicator may indicate when the contact element(s) are—or are not—in good contact with the first skin area and may prompt the user to manipulate the handpiece to restore good contact when necessary. The skin contact indicator(s) may comprise, e.g., an LED indicator on handpiece 620 that displays a first color when good skin contact exists and a second color when the window 628 is not in proper contact with the skin. Other indicators, such as an audible sound or alarm, may also be provided, and the system may be interlocked such that the system will not apply (or will terminate) a laser pulse if good contact between the cooling window 268 and the skin is absent.

Handpiece 620 further includes a temperature sensor 624 for sensing a surface temperature of the target skin area. Temperature sensor 624 may, in various embodiments, sense the temperature of the target skin area one or more times before pulse delivery (e.g., during a precooling step), during pulse delivery, or after pulse delivery (e.g., during a post-cooling step to minimize thermal damage and patient discomfort). During delivery of a therapeutic laser pulse to a target skin area, the surface temperature may be influenced by two different heating mechanisms, including energy absorbed directly from the laser, and thermal bloom resulting from energy conducted from deeper skin tissue as the thermal energy absorbed by deeper structures relaxes into the environment. Thermal bloom from deeper structures back to the skin surface may be a significant cause of epidermal damage in laser systems targeting relatively deep structures such as sebaceous or sweat glands. Therapeutic laser systems such as system 600 enable improved treatment outcomes by ensuring that the surface temperature of a target skin area remains below a desired surface temperature even while heating deeper structures to higher temperatures, minimizing both skin damage and patient discomfort.

Temperature sensor 624 may sense the surface temperature of the target skin area one or more times during the delivery of the laser pulse from diode laser 610. In various embodiments, temperature sensor 624 may be capable of sensing the surface temperature of the target skin area at from 10 to 1 million times per second. In one embodiment, the temperature sensor 624 comprises an infrared radiation detector to detect infrared energy radiating from the surface of the target skin area through the cooling window 628, and a processor (e.g., controller 640 as discussed below) to determine the surface temperature of the target skin area one or more times during a treatment pulse based on data received from the temperature sensor 624. It will be appreciated that other temperature sensors 624 may be used.

Handpiece 620 also includes a scanner 634 to sequentially direct laser pulses to different target skin areas within a first skin area in contact with cooling window 628. In some embodiments, cooling window 628 may provide contact cooling to a first skin area that is significantly larger than a single target skin area. In such embodiments, after a first target skin area is treated by a laser pulse, scanner 634 may be used to redirect subsequent pulses from the diode laser 610 to a new (i.e., second, third, etc.) target skin area for treatment within the first skin area cooled by the cooling window 628. When a desired number of target skin areas have been treated at a single cooling window position, the user may reposition the cooling window to a new position covering a new skin area, and a different group of target skin areas within the new skin area may be treated by the diode laser 610 using scanner 634. In one embodiment, scanner 634 may comprise a mirror (see FIG. 8) whose position may be adjusted on two or more axes, e.g., by one or more motors, to direct successive pulses from diode laser 610 to different target skin areas within the cooling window, enabling treatment of a relatively high proportion of the total area in contact with the cooling window. In alternative embodiments, scanner 634 may be omitted.

The system 600 further includes a controller 640, which may comprise one or more processing elements such as microprocessors, microcontrollers, field programmable gate arrays (FPGAs), etc. to control the operations of the laser treatment system. Controller 640 includes a pulse timing control unit 642 that controls the timing of the laser pulses from diode laser 610, including initiating the pulse at a first timepoint and terminating the pulse at a second timepoint. The pulse timing control unit 642 may receive data from temperature sensor 624, and may initiate the therapeutic laser pulse at a first timepoint based on, e.g., a determination that the surface temperature of the target skin area has been cooled to a desired temperature (e.g., a specific below body temperature such as 15° C., 10° C., 5° C., 0° C., –5° C., –10° C., etc.). Pulse timing control unit 642 may also terminate the therapeutic laser pulse at a second timepoint based on, e.g., a determination that the surface temperature of the target skin area has reached a threshold temperature (e.g., a surface temperature indicating that a deeper target structure such as a sebaceous gland has reached a damage threshold such as a temperature in the range of 60° C.-75° C.).

Controller 640 also includes a temperature sensing control unit 644 that controls the operation of the temperature sensor 624. In particular, temperature sensing control unit 644 ensures that the surface temperature of a target skin area is determined or measured at a desired (e.g., programmed or predetermined) sampling rate such as 10 or more times per second. Controller 640 may synchronize the operations of the temperature sensing control unit 644 with the pulse timing control unit 642.

In one embodiment, the pulse timing control unit 642 and the temperature sensing control unit 640 may comprise one or more of software, firmware, or other programming code operating in the controller 640. In one embodiment, the pulse timing control unit 642 and the temperature control unit 644 may comprise separate processors or sub-processors within controller 640. A wide variety of hardware and software designs may be used to achieve the functions described herein, and all are considered as within the scope of the present disclosure.

Controller 640 may also control other operations within the therapeutic laser treatment system 600 (e.g., software and firmware units and subunits, timers, mechanical or electrical elements or subsystems, etc.). These functions may also include, without limitation, control of the positioning of scanner 634 and thus the location within the cooling window 628 of the target skin areas. Controller 640 also controls the operation of cooling system 622, including without limitation the temperature at which the cooling window is maintained (which may be determined by a user or by the patient's skin type as described in connection with FIG. 6B), the cooling capacity (i.e., the thermal energy removal rate of the TEC), status alarms, etc.

A user interface 650 allows a system user to select or program one or more parameters (e.g., beam diameter or spot size, fluence, wavelength, target temperature of the surface of the target skin area, cooling temperature of the target skin area at which a pulse may be delivered, etc.) to direct the operation of the therapeutic laser system 600. User interface 650 also displays various status indicators and data to the user associated with the system and/or a treatment session, such as the current laser parameters, duration of treatment, number of pulses delivered, etc. Controller 640 may also receive and process inputs from the user interface 650, and may provide outputs to the user interface as well.

Finally, the system 600 includes a power supply 660 for providing power to one or more of the foregoing portions of the system. In one embodiment, power supply 660 may comprise a power supply coupled to a standard NC power outlet to convert AC to DC power at one or more voltages, and may include a battery (e.g., for backup in the event of a power outage), a supercapacitor, etc. Power supply 660 also provides power to controller 640, which in turn includes a current-controlled power supply for driving the diode laser 610 and/or other system components and subassemblies at rapid switching rates based on inputs from pulse timing control unit 642, temperature sensing control unit 644, cooling system 622, temperature sensor 24, and scanner 634.

Figure 6B:
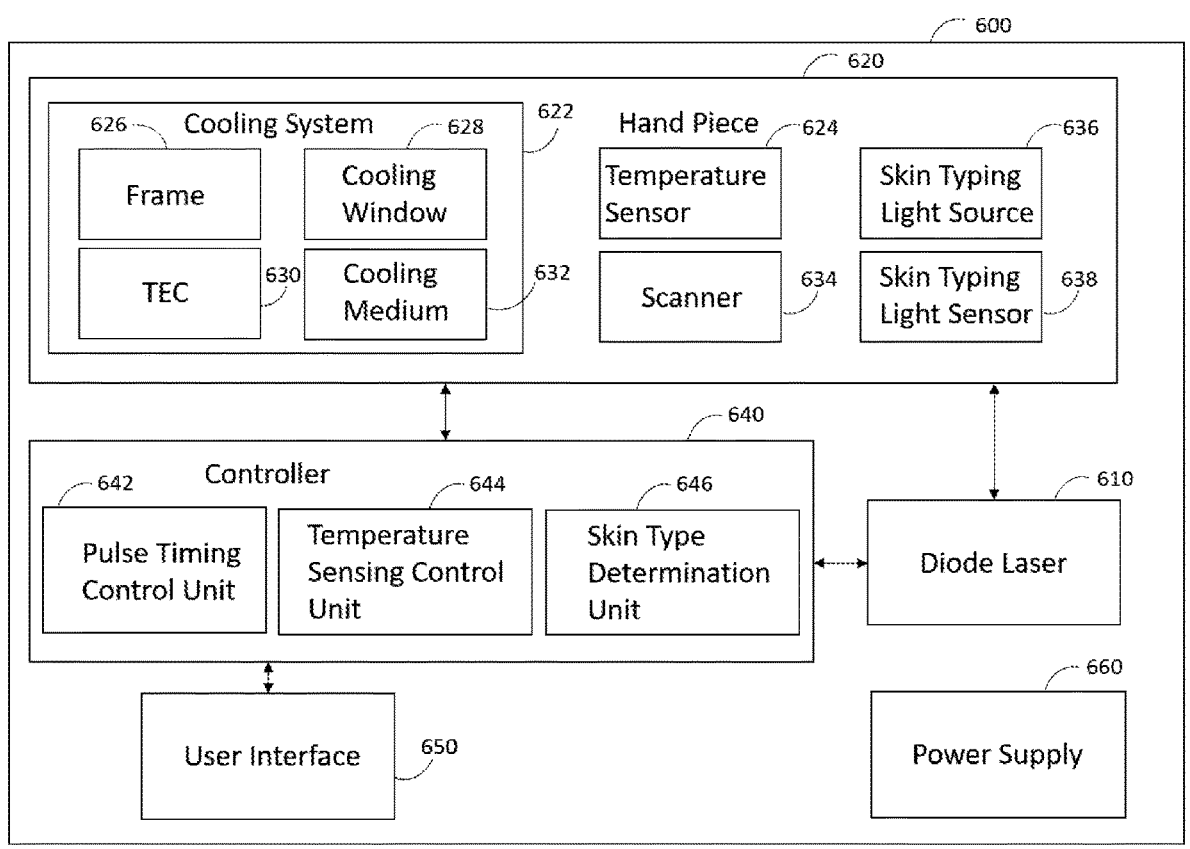

FIG. 6B is a schematic illustration of an alternative embodiment of the therapeutic laser system 600 of FIG. 6A. The therapeutic laser system of FIG. 6B provides a system capable of determining the skin type of a patient, and adjusting one or more treatment parameters based on the skin type. Like numbers are used for like elements in FIGS. 6A and 6B, and the discussion herein of FIG. 6B will omit or limit previously discussed elements of FIG. 6A for simplicity, brevity, and to avoid repetition. Elements previously described in connection with FIG. 6A will have similar functions in FIG. 6B.

The system of FIG. 6B allows one or more treatment parameters of the system 600 to be adjusted to minimize discomfort and/or pain to patients that may result from differences in skin type. Handpiece 620 includes a skin typing light source 636 for applying a multi-wavelength light signal to the skin of a patient to allow the system to determine a skin type of the patient. Although different skin typing systems may be used, in one embodiment the system 600 of FIG. 6B is adapted to determine a Fitzpatrick skin type of the patient. Skin typing light source 636 may generate noncoherent, multi-wavelength light in one or more of the visible and IR light ranges. A skin typing light sensor 638 is provided to sense a portion of the noncoherent, multi-wavelength light from light source 636 that is reflected from the skin of the patient.

Controller 640 includes a skin type determination unit 646 that receives data from the skin typing light sensor 638 relating to, e.g., the absorbance or non-absorbance of the patient's skin of particular wavelengths of light from the skin typing light source 636. The skin type determination unit 646 analyzes the absorbance/non-absorbance data from the skin typing light sensor 638 and determines a skin type of the patient. Controller 640 includes logic (not shown) to modify one or more aspects of the laser treatment based on the patient's skin type for the purpose of maintaining the skin surface temperature below a desired maximum surface temperature during treatment.

Without being bound by theory, patients with darker skin (i.e., a higher melanin content than lighter skin) may experience a more rapid temperature rise during the delivery of a laser pulse as relatively more energy from the pulse is absorbed by the more highly concentrated melanin particles in the skin. To avoid an excessive temperature (and an increased risk of patient discomfort and/or pain), controller 640 may, for example, provide additional cooling (i.e., longer cooling time) for patients with darker skin prior to applying a laser therapy; lower a target skin temperature at which a therapy pulse is initiated (e.g., initiate therapy when the skin is cooled to 5° C. for patients with darker skin instead of 10° C. for lighter-skin patients); lower a fluence of the therapeutic laser pulses to deliver less energy per unit time for darker skin patients; lower a peak power of the laser pulses of a laser therapy for darker skin patients. The controller may also modify or change other parameters such as laser pulse duration and laser spot size to ensure efficacious surface temperature control in the treatment of a wide range of skin types.

FIGS. 6A and 6B illustrate a system according to certain embodiments of the invention involving cooling the skin before, during, and after pulse delivery. However, alternative embodiments of the invention include systems with no cooling of the skin, or without cooling of the skin during one or more of the periods before, during, and after delivery of the therapeutic laser pulse. Additional alternative embodiments include systems in which different cooling capacities (i.e., rate of heat removal from the skin) are used in the periods before, during, or after delivery of the laser pulse, and during portions of these periods.

Figure 7:
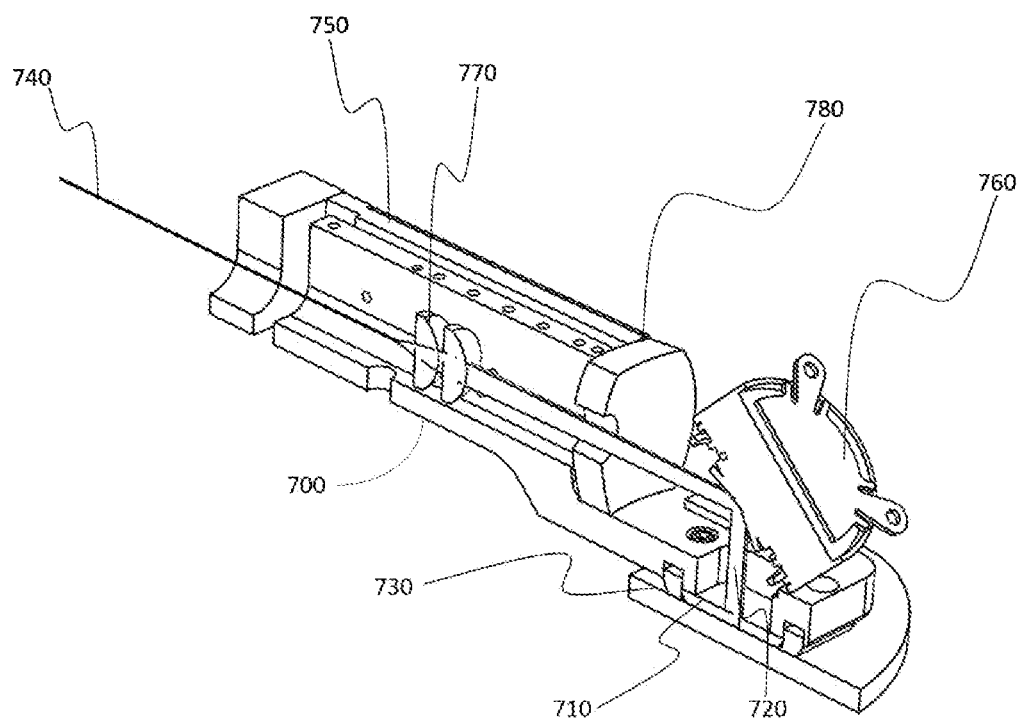
FIGS. 7 and 8 are simplified figures of a handpiece according to an embodiment of the present invention.

FIG. 7 is a simplified sectional view of the interior of a handpiece 700 for cooling a portion of a skin area 730 and applying laser pulses to one or more target skin areas, according to an embodiment of the present invention. Laser pulses, visually shown as a laser beam 720 at an instant of time, are delivered to the handpiece 700 via an optical fiber 740 from a diode laser (e.g., laser 610 of FIG. 6). After exiting optical fiber 740, pulses 720 pass through focusing lenses 770 and an aperture in a temperature detection mirror 780. Pulses 720 are redirected by a scanner 760 which may comprise a mirror, and pass through a cooling window 710 to a target skin area within a first skin area in contact with the cooling window. Scanner 760 may be controllable (e.g., by a motor) and repositionable such that one or more laser pulses 720 are sequentially directed to a series of target skin areas within the cooling window, without moving the cooling window 710 to contact a different area of skin 730.

Handpiece 700 also includes a thermoelectric cooler 750, which includes a heatsink portion 752 in contact with cooling window 710 to maintain the cooling window at a desired (e.g., programmed) temperature during contact with the first skin area. In one embodiment, cooling window 710 cools the first skin area from a first surface temperature (e.g., body temperature) to a second surface temperature before laser pulses 720 are applied to the skin. In one embodiment, the target skin area is cooled before, during, and after application of a laser pulse thereto.

Skin temperatures may be detected by infrared energy radiated from the skin through the cooling window 710. This infrared energy is reflected by scanner 760 onto temperature detector mirror 780, which focuses the infrared energy on a detection element (not shown) that enables a processor to determine the temperature of a target skin area based on the infrared energy from the detector mirror 780. Temperatures of a target skin area may be determined at a desired sampling rate as previously noted.

Figure 8:
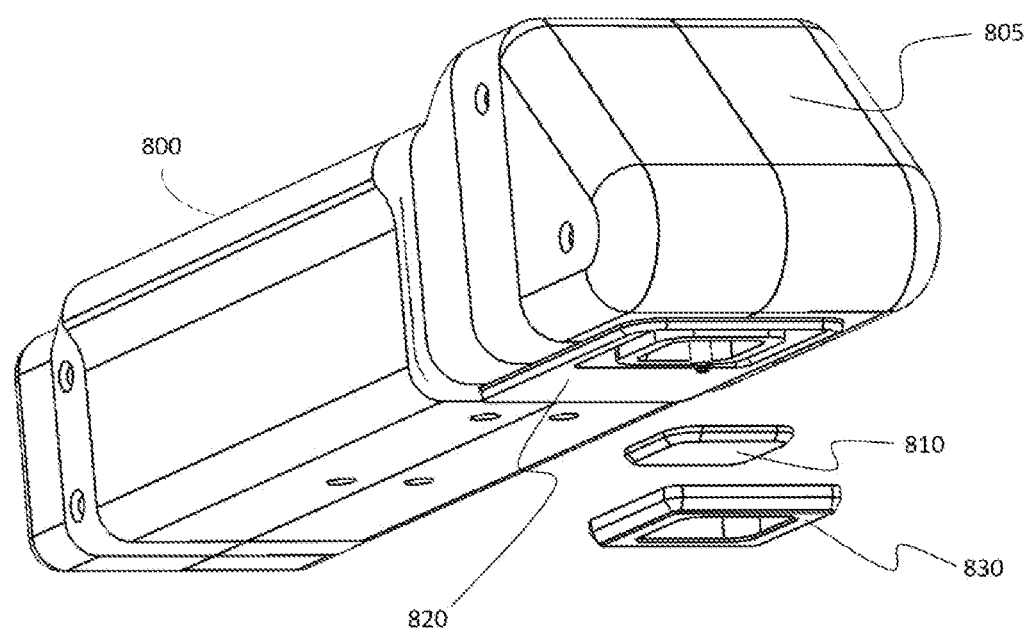

FIG. 8 is a simplified exploded and external view of a handpiece 800 for cooling skin and applying laser pulses thereto. The internal components discussed in FIG. 7 may be enclosed within a housing 805. A cooling window 810 (which may be the same as cooling window 710 of FIG. 7) is maintained in contact with a cooling heatsink 820 (which may be the same as heatsink portion 752 of TEC 750 of FIG. 7) by a window frame 830. It should be noted that window frame 830 has no thermal function and merely maintains cooling window 810 in contact with heatsink portion 820 of a TEC. It will be appreciated that additional or alternative components may be substituted for one or more of those shown in FIGS. 7 and 8, and that other similar handpiece configurations and designs may be used to practice the inventions disclosed herein, which are limited only by the claims.

In some embodiments (not shown), a handpiece may be omitted entirely, and temperature-controlled delivery of a therapeutic pulse to a target skin area may be performed with other structures to deliver the laser pulse.

Figure 9:
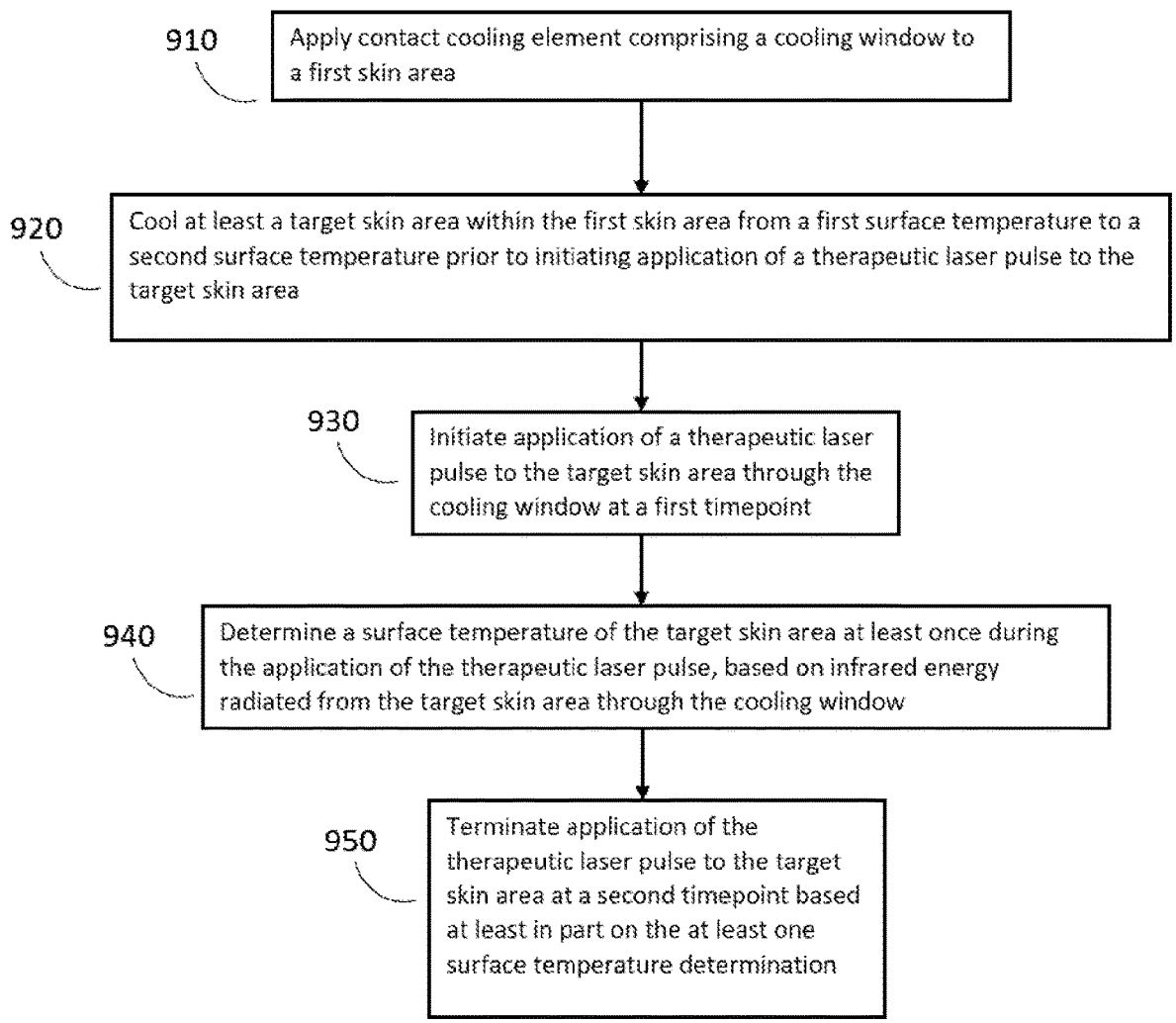
FIGS. 9-13 are flowcharts illustrating treatment methods according to various embodiments of the present invention.

FIG. 9 discloses one embodiment of a laser treatment method according to the present disclosure. The method involves the use of a contact cooling window to cool the skin of the patient to a desired temperature, and providing a therapeutic laser pulse whose duration is determined by periodic temperature determinations or measurements made during the delivery of the pulse. The temperature determinations may comprise real-time temperature measurements used by a processor to control the duration of the laser pulse (e.g., to control the temperature of a target skin area).

The method of FIG. 9 comprises applying a contact cooling element to a first skin area (910). The contact cooling element comprises a cooling window, such as cooling window 628 (FIGS. 6A, 6B) to contact the first skin area. In one embodiment, the cooling window is cooled to a reservoir temperature below a first skin temperature of the skin prior to contact with the cooling window. The cooling window is then moved into contact, with the skin (preferably direct contact), and cools the skin from a first temperature to a second temperature below the first temperature. In preferred embodiments, the reservoir temperature is a temperature sufficiently below the second temperature to provide a temperature difference with the skin to enable sufficient heat flux through the cooling window to cool the surface of the skin to the second temperature relatively quickly, e.g., 10 sec or less, preferably 5 second or less, more preferably 3 seconds or less, more preferably about 2 seconds.

Referring again to FIG. 9, the method further comprises cooling at least a target skin area within the first skin area from a first surface temperature to a second surface temperature prior to initiating application of a therapeutic laser pulse to the target skin area (920). The application of a therapeutic laser pulse to the target skin area through the cooling window is initiated at a first timepoint (930). The method further comprises determining a surface temperature of the target skin area at least one during the application of the therapeutic laser pulse, based on infrared energy radiated from the target skin area through the cooling window (940).

In preferred, embodiments, a plurality of surface temperature determinations are made during the delivery of the pulse. From the plurality of surface temperature determinations, a linear or polynomial fit to the temperature data may be used to determine a rate of increase of the skin temperature caused by the delivery of the laser energy to the target skin area. In one embodiment, the line or polynomial may be used to identify a future timepoint at which a desired temperature will be reached.

Finally, the method of FIG. 9 includes terminating application of the therapeutic laser pulse to the target skin area at a second timepoint based at least in part on the at least one surface temperature determination (950). In different embodiments, the second timepoint may comprise a timepoint at which a temperature determination indicates that the surface skin temperature of the target skin area has reached or slightly exceeded a desired second temperature, or a timepoint predicted from a linear or polynomial fit to prior temperature determination data as discussed above.

Figure 10:
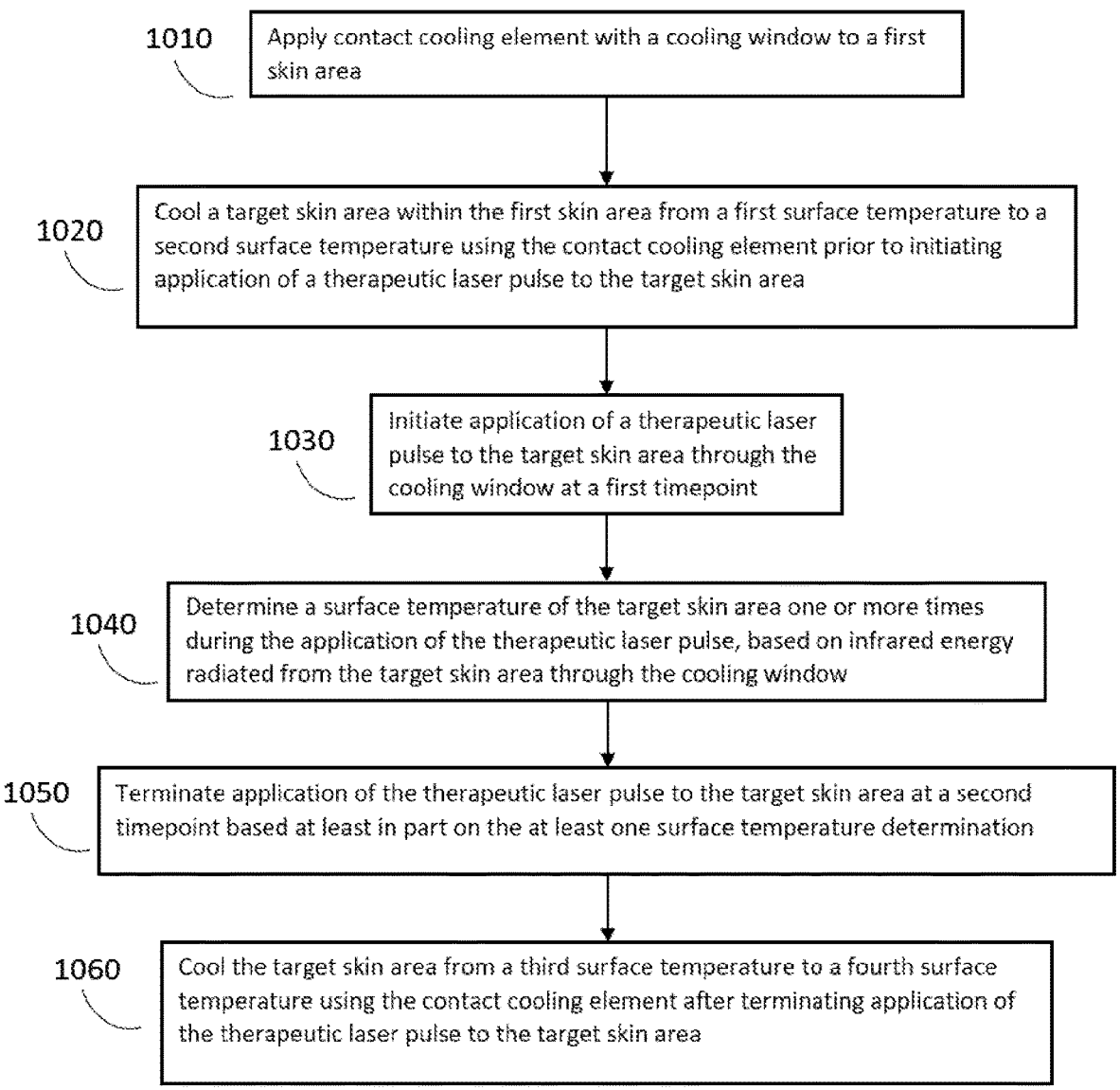

FIG. 10 discloses another embodiment of a method according to the present invention. The method comprises applying a contact cooling element with a cooling window to a first skin area (1010). The method further comprises at least one cooling step, which may comprise either or both of a cooling step prior to initiating, or after terminating, the application of a therapeutic laser pulse to a target skin area within the first skin area. In the former case, the method comprises cooling a target skin area within the first skin area from a first surface temperature to a second surface temperature using the contact cooling element prior to initiating the application of a therapeutic laser pulse to the target skin area (1020). In the latter case, the method comprises cooling the target skin area from a third surface temperature (e.g., a temperature of the surface of the target skin areas at the moment of terminating a therapeutic laser pulse) to a fourth surface temperature (e.g., a desired temperature below the third temperature, such as 50° C., 45° C., 40° C., or body temperature) using the contact cooling element after terminating application of the therapeutic laser pulse to the target skin area (1060). In one embodiment of the invention, step 1020 is omitted and step 1060 is performed. In one embodiment, step 1020 is included in the method and step 1060 is omitted. In a still further embodiment, both steps 1020 and 1060 are performed.

Referring again to FIG. 10, the method further comprises initiating the application of a therapeutic laser pulse to the target skin area through the cooling window at a first timepoint (1030). After the therapeutic laser pulse is initiated, the method comprises determining a surface temperature of the target skin area one or more times during the application of the therapeutic laser pulse, based on infrared energy radiated from the target skin area through the cooling window (1040). In preferred embodiments, a plurality of surface temperature determinations is made during the delivery of the pulse at step 1040. In these embodiments, a linear or polynomial fit to the temperature data may be performed and used to identify (e.g., predict) a future timepoint at which a desired temperature will be reached.

Finally, the method includes terminating the application of the therapeutic laser pulse to the target skin area at a second timepoint based at least in part on the at least one surface temperature determination (1050). In different embodiments, the second timepoint may comprise a timepoint at which a temperature determination indicates that the surface skin temperature of the target skin area has reached or slightly exceeded a desired second temperature, or a timepoint predicted from a linear or polynomial fit to prior temperature determination data as discussed above.

Figure 11:
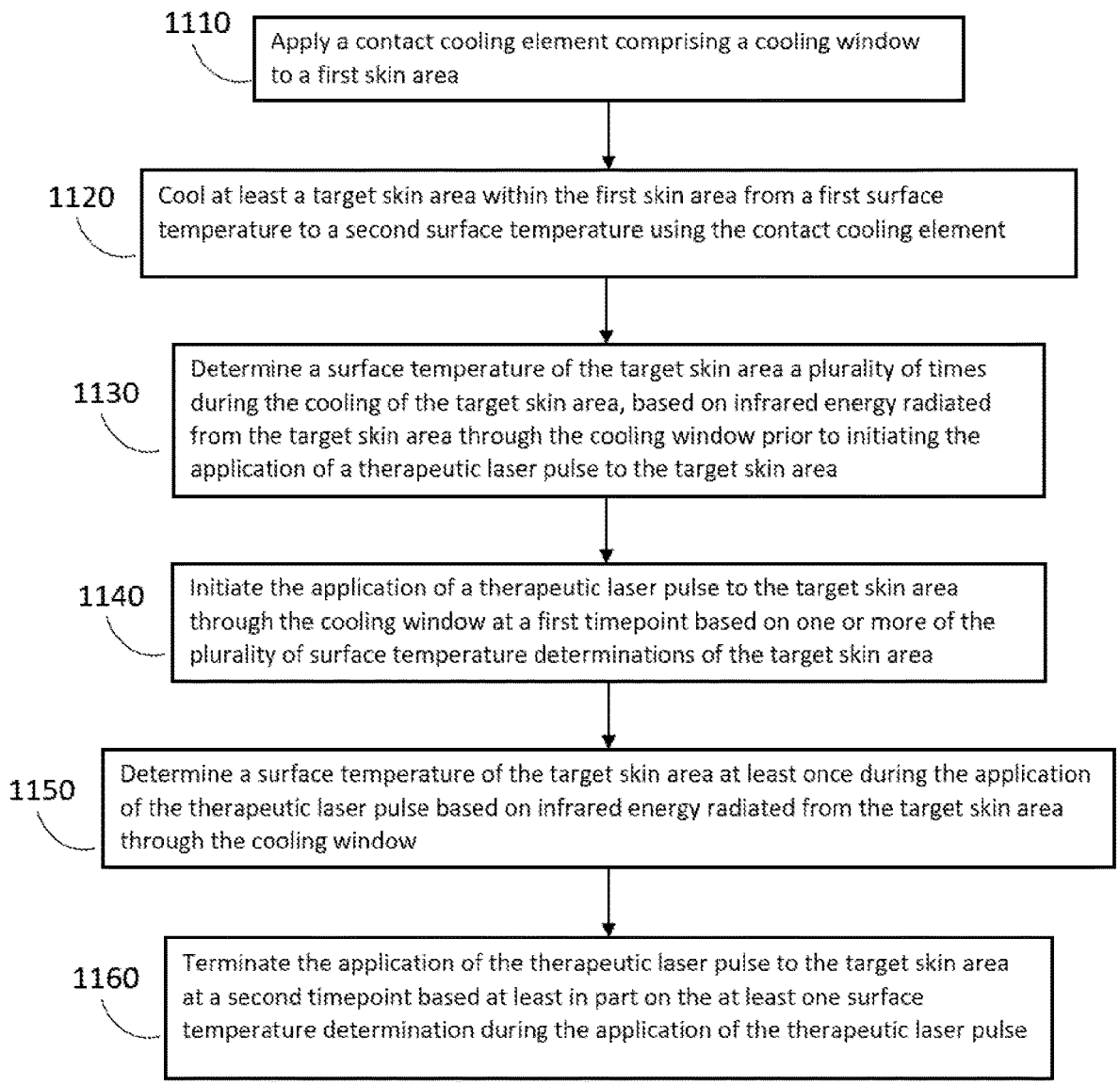

FIG. 11 discloses another embodiment of a method according to the present invention. The method comprises applying a contact cooling element having a cooling window to a first skin area (1110), and cooling at least a target skin area within the first skin area from a first surface temperature to a second surface temperature using the contact cooling element (1120). In one embodiment, step 1120 comprises cooling the surface temperature of the target skin area from body temperature (e.g., 36.5-37.5° C.) to a lower temperature (e.g., a temperature within the range of −10° C. to 20° C.) that may vary depending upon factors such as the depth of the target structure to be treated with the laser, and the maximum desired temperature for the tissue overlying the target structure.

The method further comprises determining, prior to initiating the application of a therapeutic laser pulse to the target skin area, a surface temperature of the target skin area a plurality of times during the cooling of the target skin area, based on infrared energy radiated from the target skin area through the cooling window (1130). As discussed in connection with FIGS. 6A, 7 and 8, in one embodiment the temperature may be determined by a temperature sensing control unit (e.g., 644, FIG. 6), which processes temperature sensing data from a temperature sensor (e.g., a temperature sensing mirror 780, FIG. 7) focusing infrared energy on a detection element such as a photodiode having a desired sampling interval, e.g., 0.5-2.0 msec. In one embodiment, the photodiode is sensitive to light within a wavelength range of from about 2-40 microns and is insensitive to light at the laser wavelength range. In other embodiments, a CCD (charge-coupled device) or CMOS (complementary metal oxide semiconductor) light sensor may be used as the detection element. In a particular embodiment, the detection element may comprise at model IR1011 sensor, available from AKM Semiconductor, Inc., San Jose, Calif., although it will be appreciated that other sensors may be used in different embodiments. The detection element may be selected based in part on the material used for the cooling window 1130. Regardless of the type of temperature sensing structure(s) used to sense the surface temperature of the target skin area, the temperature determinations are performed a plurality of times from infrared energy radiated through the cooling window.

Referring again to FIG. 11, the method further comprises, at step 1140, initiating the application of a therapeutic laser pulse to the target skin area through the cooling window at a first timepoint, where the first timepoint is based on one or more of the plurality of surface temperature determinations from step 1130. In one embodiment, the first timepoint may be a timepoint at which a surface temperature determination indicates that the target skin area has been cooled to the second surface temperature. In one embodiment, the first timepoint may be a predicted timepoint, based on one or more of the temperature determinations, of when the target skin area will reach the second surface temperature.

After the therapeutic laser pulse is initiated, the method comprises determining a surface temperature of the target skin area at least once during the application of the therapeutic laser pulse, based on infrared energy radiated from the target skin area through the cooling window (1150). In preferred embodiments, a plurality of surface temperature determinations is made during the delivery of the therapeutic laser pulse.

Finally, the method includes terminating the application of the therapeutic laser pulse to the target skin area at a second timepoint based at least in part on the at least one surface temperature determination during the application of the therapeutic laser pulse (1160). In different embodiments, the second timepoint may comprise a timepoint at which a temperature determination indicates that the surface skin temperature of the target skin area has reached or slightly exceeded a desired temperature, or a timepoint predicted from a linear or polynomial fit to prior temperature determinations made during the delivery of the therapeutic laser pulse.

Figure 12:
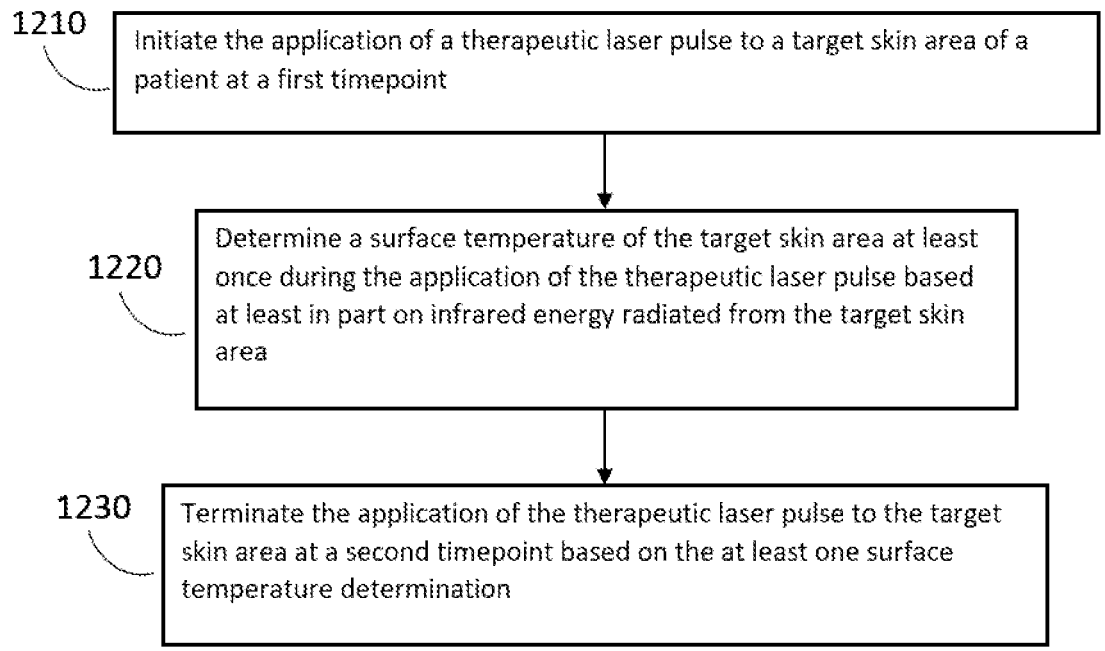

In one aspect, the invention comprises methods of treating a patient by controlling the duration of a laser pulse without a required cooling step. FIG. 12 discloses one embodiment of such a method. The method comprises initiating the application of a therapeutic laser pulse to a target skin area of a patient at a first timepoint (1210). After the pulse is initiated, the method further includes determining a surface temperature of the target skin area at least once during the application of the therapeutic laser pulse based at least in part on infrared energy radiated from the target skin area (1220). The determination(s) of surface temperature may, in one embodiment, be performed as described in the discussion of FIG. 11. Finally, the method includes terminating the application of the therapeutic laser pulse to the target skin area at a second timepoint based on the at least one surface temperature determination (1230).

Figure 13:
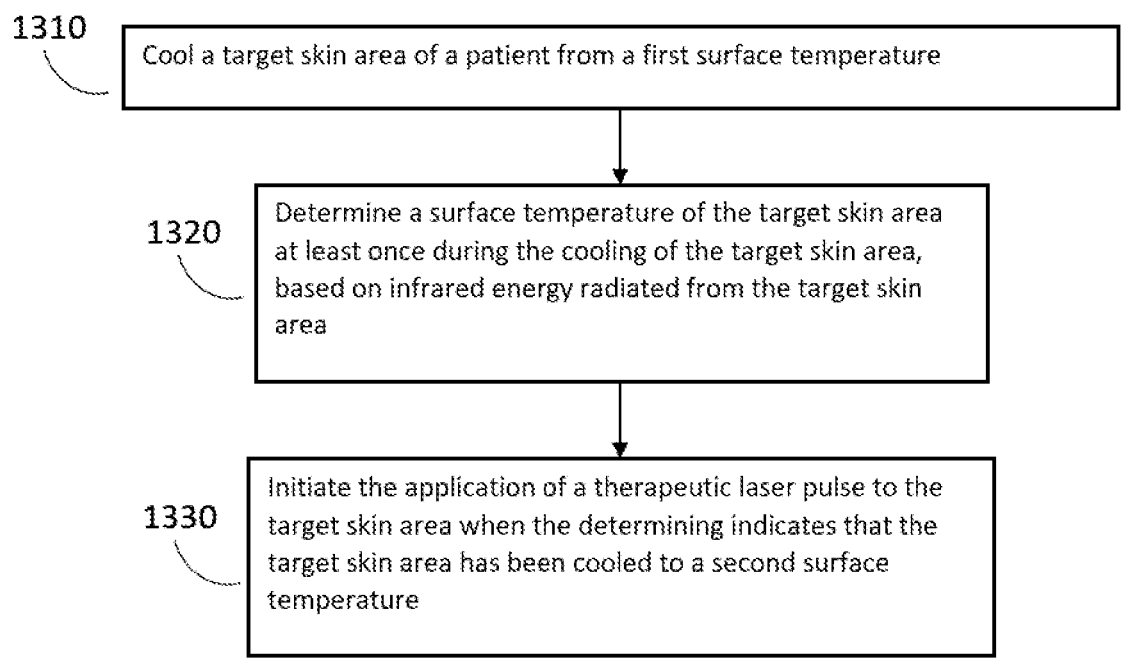

In one aspect, the invention comprises methods of treating a patient by initiating a therapeutic laser pulse when the skin has been pre-cooled to a desired temperature. FIG. 13 discloses one embodiment of such a method. The method comprises cooling a target skin area of a patient from a first surface temperature (1310), and determining a surface temperature of the target skin area at least once during the cooling of the target skin area based on infrared energy radiated from the target skin area (1320). Finally, the method comprises initiating the application of a therapeutic laser pulse to the target skin area when the determining step (i.e., step 1320) indicates that the target skin area has been cooled to a second surface temperature.

In various embodiments, the present invention relates to the subject matter of the following numbered paragraphs.

101. A method of controlling a duration of a therapeutic laser pulse to the skin of a patient, the method comprising:
initiating, at a first timepoint, the application of a therapeutic laser pulse to a target skin area of the patient;
determining a surface temperature of the target skin area at least once during the application of the therapeutic laser pulse based at least in part on infrared energy radiated from the target skin area; and
terminating the application of the therapeutic laser pulse to the target skin area at a second timepoint based on the at least one surface temperature determination.

102. The method of claim 101, further comprising:
applying a contact cooling element comprising a cooling window to a first skin area proximate to the target skin area; and
cooling at least the target skin area from a first surface temperature to a second surface temperature.

103. The method of claim 102, wherein the cooling window comprises a material selected from sapphire, ZnS, diamond, ZnSe, and a different thermally conductive material that is transmissive to infrared light.

104. The method of claim 102, wherein the step of cooling at least the target skin area to the second surface temperature is performed prior to initiating the application of the therapeutic laser pulse to the target skin area.

105. The method of claim 102, wherein cooling at least the target skin area comprises cooling the cooling window using a cooling medium selected from the group consisting of water, a halogenated hydrocarbon refrigerant, and air.

106. The method of claim 102, wherein cooling at least the target skin area comprises cooling the cooling window using a thermoelectric cooler.

107. The method of claim 101, further comprising cooling at least the target skin area from a first surface temperature to a second surface temperature.

108. The method of claim 107, wherein cooling at least the target skin area comprises cooling at least the target skin area, prior to initiating the application of the therapeutic laser pulse, from a first surface temperature of body temperature to a second surface temperature within the range of −10° C. to 20° C.

109. The method of claim 107, wherein cooling at least the target skin area comprises cooling at least the target skin area, prior to initiating the application of the therapeutic laser pulse, from a first surface temperature to a second surface temperature within the range of −5° C. to 10° C.

110. The method of claim 107, wherein cooling at least a target skin area comprises cooling the surface of the target skin area, prior to initiating the application of the therapeutic laser pulse, from a first surface temperature to a second surface temperature within the range of −5° C. to 5° C.

111. The method of claim 107, wherein cooling at least the target skin area comprises one of
cooling the target skin area from the first surface temperature to the second surface temperature prior to initiating the application of the therapeutic laser pulse; and
cooling the target skin area from the first surface temperature to the second surface temperature after terminating the application of the therapeutic laser pulse.

112. The method of claim 107, wherein cooling at least the first target skin area from a first surface temperature to a second surface temperature comprises cooling the target skin area to the second surface temperature prior to initiating the application of the therapeutic laser pulse, the method further comprising
cooling the target skin area from a third surface temperature to a fourth surface temperature after terminating the application of the therapeutic laser pulse.

113. The method of claim 112, wherein the third surface temperature is user-selectable.

114. The method of claim 112, wherein at least one of the third surface temperature and the fourth surface temperature is user-selectable.

115. The method of claim 101, further comprising:
determining the pulse duration of the therapeutic laser pulse as the difference between the first and second timepoint;
applying a subsequent therapeutic laser pulse to the of controlling a duration of a therapeutic laser pulse to the skin of a patient, the method comprising:
initiating, at a first timepoint, the application of a therapeutic laser pulse to a target skin area of the patient;
determining a surface temperature of the target skin area at least once during the application of the therapeutic laser pulse based at least in part on infrared energy radiated from the target skin area; and
terminating the application of the therapeutic laser pulse to the target skin area at a second timepoint based on the at least one surface temperature determination.

116. The method of claim 101, wherein determining a surface temperature of the target skin area at least once during the application of the therapeutic laser pulse comprises determining a surface temperature of the target skin area a plurality of times during the application of the therapeutic laser pulse at a predetermined temperature sampling time interval of 100 msec or less.

117. The method of claim 116, wherein the predetermined temperature sampling time interval is a time interval within the range of 0.01-10.0 msec.

118. The method of claim 101, wherein initiating the application of a therapeutic lase pulse comprises initiating a laser pulse at a power density of at least 100 W/cm2.

119. The method of claim 101, wherein initiating the application of a therapeutic laser pulse comprises initiating a laser pulse having an energy fluence of at least 2 J/cm2.

120. The method of claim 119, wherein the therapeutic laser pulse has an energy fluence within the range of 2-100 J/cm2.

121. The method of claim 120, wherein the therapeutic laser pulse has an energy fluence within the range of 2-40 J/cm2.

201. A method of treating the skin of a patient with a therapeutic laser pulse, the method comprising:
   a) applying a contact cooling element comprising a cooling window to a first skin area of the patient;
   b) cooling at least a target skin area within the first skin area from a first surface temperature using the contact cooling element;
   c) determining a surface temperature of the target skin area a plurality of times during the application of the contact cooling element to the first skin area, wherein each of said surface temperature determinations is based on infrared energy radiated from the target skin area through the cooling window prior to initiating the application of a therapeutic laser pulse to the target skin area;
   d) initiating the application of a therapeutic laser pulse to the target skin area through the cooling window at a first timepoint based at least in part on one or more of the plurality of surface temperature determinations of the target skin area.

202. The method of claim 201, further comprising:
   e) determining a surface temperature of the target skin area at least once during the application of the therapeutic laser pulse, based on infrared energy radiated from the target skin area through the cooling window; and
   f) terminating the application of the therapeutic laser pulse to the target skin area at a second timepoint based on the at least one surface temperature determination.

301. A method of treating the skin of a patient with a therapeutic laser pulse, the method comprising:
   a) cooling a target skin area of the patient from a first surface temperature;
   b) determining a surface temperature of the target skin area a plurality of times during the cooling of the target skin area, wherein the determining is based on infrared energy radiated from the target skin area;
   c) initiating the application of a therapeutic laser pulse to the target skin area when the determining indicates that the target skin area has been cooled to a second surface temperature.

302. The method of claim 301, further comprising:
   d) determining a surface temperature of the target skin area a plurality of times during the application of the therapeutic laser pulse to the target skin area, wherein the determining is based on infrared energy radiated from the target skin area.

303. The method of claim 301, further comprising:
   d) characterizing the patient's skin; and
   e) determining a target second surface temperature based on the characterizing.

304. The method of claim 303, wherein characterizing the patient's skin comprises determining a melanin content of at least a portion of the patient's skin, and wherein determining a target second surface temperature comprises selecting a lower target second surface temperature the higher the patient's melanin content.

305. The method of claim 303, wherein characterizing the patient's skin comprises determining a Fitzpatrick score indicative of the skin type of the patient, and wherein determining a second target surface temperature comprises selecting a lower target second surface temperature for higher Fitzpatrick scores.

The particular embodiments disclosed and discussed above are illustrative only, as the invention may be modified and practiced in different but equivalent manners apparent to those skilled in the art having the benefit of the teachings herein. Embodiments of the present invention disclosed and claimed herein may be made and executed without undue experimentation with the benefit of the present disclosure. While the invention has been described in terms of particular embodiments, it will be apparent to those of skill in the art that variations may be applied to systems and apparatus described herein without departing from the concept, spirit and scope of the invention. Examples are all intended to be non-limiting. It is therefore evident that the particular embodiments disclosed above may be altered or modified and all such variations are considered within the scope and spirit of the invention, which are limited only by the scope of the claims.

What is claimed is:
1. A method of treating the skin of a patient with a therapeutic laser pulse, the method comprising:
   a) initiating the application of a therapeutic laser pulse to a target skin area at a first timepoint;
   b) determining a surface temperature of the target skin area a plurality of times, at a temperature sampling interval of 100 msec or less, during the application of the therapeutic laser pulse to the target skin area based on infrared energy radiated from the target skin area; and
   c) terminating the application of the therapeutic laser pulse to the target skin area at a second timepoint based at least in part on the plurality of surface temperature determinations, wherein each of the plurality of surface temperature determinations occurs during a single therapeutic laser pulse having a pulse duration comprising the period from the first timepoint to the second timepoint.

2. The method of claim 1, wherein the temperature sampling interval is an interval within the range of 0.01-10.0 msec.

3. The method of claim 1, further comprising:
   d) applying a contact cooling element comprising a cooling window to a first skin area, wherein the target skin area is within the first skin area, wherein the cooling window comprises a thermally conductive material that is transmissive to infrared energy and to the therapeutic laser pulse; and
   e) performing at least one cooling action selected from
      1) Cooling the target skin area from a first surface temperature to a second surface temperature using the contact cooling element prior to initiating the application of the therapeutic laser pulse to the target skin area;
      2) Cooling the target skin area during the delivery of the therapeutic laser pulse; and 3) cooling the target skin area from a third surface temperature at the termination of the therapeutic laser pulse to a fourth surface temperature using the contact cooling element.

4. The method of claim 3, wherein performing at least one cooling action comprises cooling the cooling window using a thermoelectric cooler (TEC) thermally coupled to the cooling window.

5. The method of claim 3, wherein the cooling window comprises a material selected from sapphire, ZnS, diamond, and ZnSe.

6. The method of claim 3, further comprising:
f) determining a surface temperature of the target skin area a plurality of times, at a temperature sampling interval of 100 msec or less and based on infrared energy radiated from the target skin area, during the step of performing at least one cooling action.

7. The method of claim 6, wherein performing at least one cooling action comprises cooling the target skin area within the first skin area, prior to initiating the application of the therapeutic laser pulse, from a first surface temperature of body temperature to a second surface temperature within the range of −10° C. to 20° C.

8. The method of claim 1, wherein terminating the application of the therapeutic laser pulse comprises terminating the application of the therapeutic laser pulse when at least one of the plurality of surface temperature determinations indicates that the target skin area has reached a target treatment temperature.

9. The method of claim 8, wherein the target treatment temperature is a user-selectable temperature in the range of 35° C. to 85° C.

10. The method of claim 1, wherein the time interval between the first timepoint and the second timepoint is a time interval within the range of 0.01-200 msec.

11. The method of claim 1, wherein initiating the application of a therapeutic laser pulse comprises initiating a laser pulse from a diode laser, and wherein the therapeutic laser pulse has an energy fluence of at least 2 J/cm2.

12. The method of claim 1, wherein initiating the application of a therapeutic laser pulse comprises initiating the application of optical energy having a wavelength within a range of from about 1700 nm to about 1740 nm.

13. The method of claim 1, wherein the therapeutic laser pulse has an energy fluence within the range of 2-100 J/cm2.

* * * * *